US009594081B2

(12) United States Patent
Alderman et al.

(10) Patent No.: US 9,594,081 B2
(45) Date of Patent: Mar. 14, 2017

(54) METHODS AND SYSTEMS FOR THE RAPID CHARACTERIZATION OF FUNCTIONAL BIOLOGICAL MOLECULES

(75) Inventors: Edward Marshall Alderman, Framingham, MA (US); Brett Peter Masters, Belmont, CA (US); Michael Francis Miller, Hollis, NH (US); William Matthew Dickerson, Dorchester, MA (US)

(73) Assignee: ProterixBio, Inc., Billerica, MA (US)

( * ) Notice: Subject to any disclaimer, the term of this patent is extended or adjusted under 35 U.S.C. 154(b) by 218 days.

(21) Appl. No.: 14/128,193

(22) PCT Filed: Jun. 20, 2012

(86) PCT No.: PCT/US2012/043341
§ 371 (c)(1),
(2), (4) Date: Aug. 11, 2014

(87) PCT Pub. No.: WO2012/177755
PCT Pub. Date: Dec. 27, 2012

(65) Prior Publication Data
US 2015/0031047 A1    Jan. 29, 2015

Related U.S. Application Data

(60) Provisional application No. 61/499,079, filed on Jun. 20, 2011, provisional application No. 61/542,513, (Continued)

(51) Int. Cl.
| | | |
|---|---|---|
| G01N 33/543 | (2006.01) | |
| G01N 29/02 | (2006.01) | |
| G01N 27/74 | (2006.01) | |

(52) U.S. Cl.
CPC ..... *G01N 33/54393* (2013.01); *G01N 27/745* (2013.01); *G01N 29/022* (2013.01);
(Continued)

(58) Field of Classification Search
CPC .......... G01N 33/54393; G01N 27/745; G01N 29/022; G01N 33/54333; G01N 33/54373
See application file for complete search history.

(56) References Cited

U.S. PATENT DOCUMENTS

| | | | |
|---|---|---|---|
| 4,279,885 A | 7/1981 | Reese et al. | ...................... 424/1 |
| 4,668,621 A | 5/1987 | Doellgast | ........................ 435/13 |

(Continued)

OTHER PUBLICATIONS

Dickerson et al., "Developing Custom Chinese Hamster Ovary-host Cell Protein Assays using Acoustic Membrane Microparticle Technology," *J. Vis. Exp.*, vol. 48, 7 pages (Feb. 2011) Accessed online—<URL:http://www.jove.com/video/2493/developing-custom-chinese-hamster-ovary-host-cell-protein-assays>, 8 pages, entire document.

(Continued)

*Primary Examiner* — Melanie Y Brown
(74) *Attorney, Agent, or Firm* — Sunstein Kann Murphy & Timbers LLP

(57) ABSTRACT

In one non-limiting aspect, the invention provides a method for detecting the quality of a biological molecule comprising forming a first mixture of ingredients comprising: (i) a first binding agent that specifically binds to a tag, wherein the first binding agent is attached to a solid support; (ii) a decoy comprising a first portion comprising the tag attached to a second portion comprising an anchor; (iii) a sensor attached to a second binding agent that specifically binds to the anchor; and (iv) a sample suspected of containing a high quality biological molecule comprising a tag, wherein the tag of the high quality biological molecule is accessible; allowing interaction of the ingredients such that the sensor provides an output signal.

20 Claims, 19 Drawing Sheets

Related U.S. Application Data filed on Oct. 3, 2011, provisional application No. 61/594,562, filed on Feb. 3, 2012, provisional application No. 61/609,099, filed on Mar. 9, 2012.

(52) U.S. Cl.
CPC . *G01N 33/54333* (2013.01); *G01N 33/54373* (2013.01); *G01N 2446/20* (2013.01)

(56) References Cited

U.S. PATENT DOCUMENTS

| | | | |
|---|---|---|---|
| 6,350,452 B1 | 2/2002 | Riss | 424/185.1 |
| 7,648,844 B2 | 1/2010 | Srivastava et al. | 436/526 |
| 7,745,158 B2 | 6/2010 | Phillips et al. | 435/7.31 |
| 2002/0152037 A1* | 10/2002 | Sunshine | G01N 29/022 702/23 |
| 2004/0029135 A1 | 2/2004 | Ramberg | 435/6 |
| 2005/0064485 A1* | 3/2005 | Vogel | G01N 21/6428 435/6.11 |
| 2007/0224700 A1* | 9/2007 | Masters | B01L 3/502761 436/501 |
| 2009/0068759 A1 | 3/2009 | Arenas et al. | 436/518 |
| 2013/0034847 A1* | 2/2013 | Kojic | C12Q 1/6804 435/6.1 |

OTHER PUBLICATIONS

Yan et al., "Analysis of two pharmacodynamic biomarkers using acoustic micro magnetic particles on the ViBE bioanalyzer," *Analytical Biochemistry*, vol. 410, pp. 13-18 (Nov. 2010).

Blaine R. Copenheaver, Authorized officer United States Patent and Trademark Office Attn: Mail Stop PCT, International Search Report—Application No. PCT/US2012/043341, dated Oct. 19, 2012 (3 pages).

Athina Nickitas-Etienne, Authorized officer The International Bureau of WIPO, International Preliminary Report on Patentability—Application No. PCT/US2012/043341, dated Dec. 23, 2013 (12 pages).

* cited by examiner

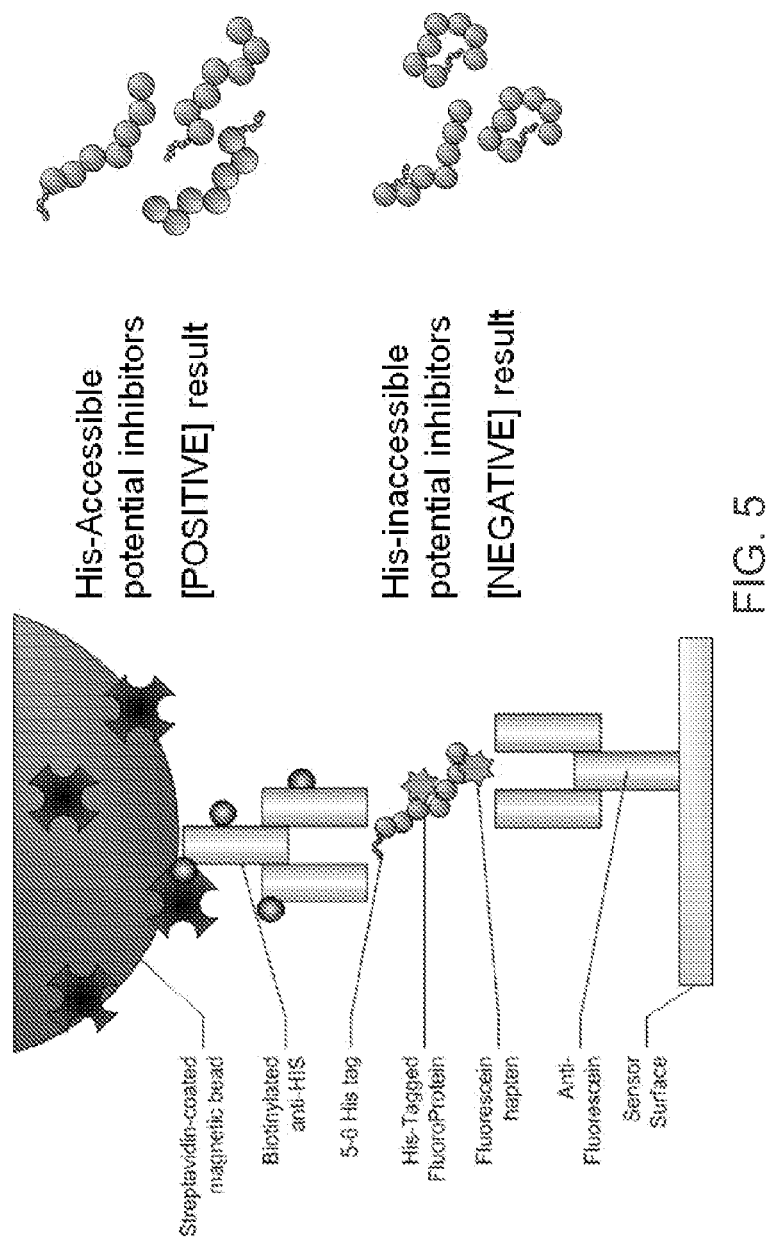

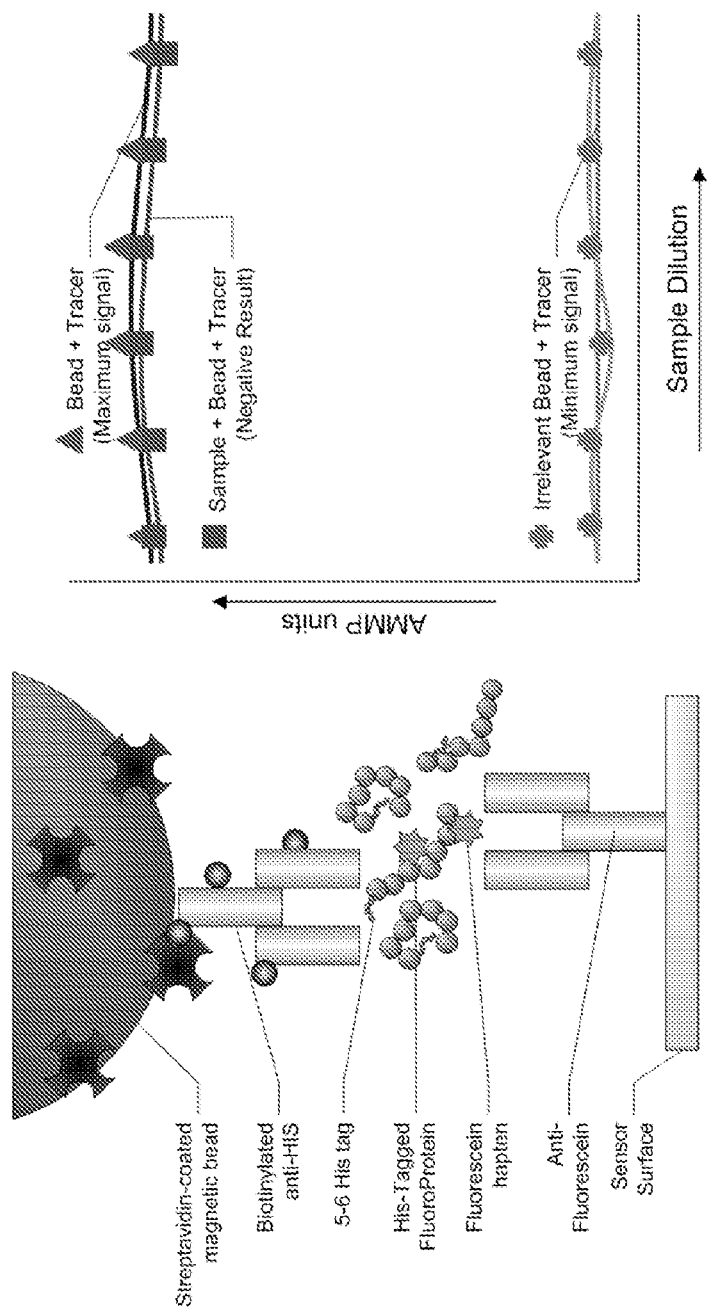

SEQUENCE LISTING

```
<160> NUMBER OF SEQ ID NOS: 8

<210> SEQ ID NO 1
<211> LENGTH: 125
<212> TYPE: PRT
<213> ORGANISM: Homo sapiens

<400> SEQUENCE: 1

Met Ala Gly Pro Ser Leu Ala Cys Cys Leu Leu Gly Leu Leu Ala Leu
1               5                   10                  15

Thr Ser Ala Cys Tyr Ile Gln Asn Cys Pro Leu Gly Gly Lys Arg Ala
            20                  25                  30

Ala Pro Asp Leu Asp Val Arg Lys Cys Leu Pro Cys Gly Pro Gly Gly
```

-continued

```
                    35                  40                  45
Lys Gly Arg Cys Phe Gly Pro Asn Ile Cys Cys Ala Glu Glu Leu Gly
         50                  55                  60

Cys Phe Val Gly Thr Ala Glu Ala Leu Arg Cys Gln Glu Glu Asn Tyr
 65                  70                  75                  80

Leu Pro Ser Pro Cys Gln Ser Gly Gln Lys Ala Cys Gly Ser Gly Gly
                 85                  90                  95

Arg Cys Ala Val Leu Gly Leu Cys Cys Ser Pro Asp Gly Cys His Ala
            100                 105                 110

Asp Pro Ala Cys Asp Ala Glu Ala Thr Phe Ser Gln Arg
            115                 120                 125

<210> SEQ ID NO 2
<211> LENGTH: 8
<212> TYPE: PRT
<213> ORGANISM: Artificial Sequence
<220> FEATURE:
<223> OTHER INFORMATION: Synthetic

<400> SEQUENCE: 2

Asp Tyr Lys Asp Asp Asp Asp Lys
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic

<400> SEQUENCE: 3

Tyr Pro Tyr Asp Val Pro Asp Tyr Ala
1               5

<210> SEQ ID NO 4
<211> LENGTH: 14
<212> TYPE: PRT
<213> ORGANISM: Artificial Sequence
<220> FEATURE:
<223> OTHER INFORMATION: Synthetic

<400> SEQUENCE: 4

Gly Lys Pro Ile Pro Asn Pro Leu Leu Gly Leu Asp Ser Thr
1               5                  10

<210> SEQ ID NO 5
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(9)
<223> OTHER INFORMATION: corresponds to residues 4-12 of seq id no. 4

<400> SEQUENCE: 5

Ile Pro Asn Pro Leu Leu Gly Leu Asp
1               5

<210> SEQ ID NO 6
<211> LENGTH: 10
<212> TYPE: PRT
<213> ORGANISM: Artificial Sequence
<220> FEATURE:
```

```
<223> OTHER INFORMATION: Synthetic

<400> SEQUENCE: 6

Glu Gln Lys Leu Ile Ser Glu Glu Asp Leu
1               5                   10

<210> SEQ ID NO 7
<211> LENGTH: 9
<212> TYPE: PRT
<213> ORGANISM: Artificial Sequence
<220> FEATURE:
<223> OTHER INFORMATION: Synthetic

<400> SEQUENCE: 7

Cys Tyr Ile Gln Asn Cys Pro Leu Gly
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic

<400> SEQUENCE: 8

Cys Tyr Phe Gln Asn Cys Pro Arg Gly
1               5
```

METHODS AND SYSTEMS FOR THE RAPID CHARACTERIZATION OF FUNCTIONAL BIOLOGICAL MOLECULES

CROSS REFERENCE TO RELATED APPLICATION

This application is a US national stage entry under 35 USC §371 of PCT Application No. PCT/US2012/043341 filed Jun. 20, 2012 which claims priority to U.S. Provisional Application Ser. No. 61/499,079 filed Jun. 20, 2011, and to U.S. Provisional Application Ser. No. 61/542,513, filed Oct. 3, 2011, and to U.S. Provisional Application Ser. No. 61/594,562 filed Feb. 3, 2012 and to U.S. Provisional Application Ser. No. 61/609,099 filed Mar. 9, 2012, the entire contents of which applications are hereby incorporated by reference.

BACKGROUND OF THE INVENTION

The invention relates to the field of biology.

With the emergence of biologicals as therapeutic reagents in the pharmaceutical industry, there is a need to efficiently determine the quantity and quality of biological molecules such as proteins, lipids, carbohydrates, etc. For example, the proper conformation and/or proper processing of a recombinantly produced biological molecule (including, for example, proper folding or proper secondary modification) is important to the ability of the biological molecule to function in vivo.

Unfortunately, the given the large size and complexity of biological molecules, such measurements are difficult to obtain. Without a simple method for consistently and accurately measuring proteins, advances in the field are hampered.

Accordingly, there is a need for developing methods and systems for identifying correctly folded biological molecules.

SUMMARY OF THE INVENTION

Recombinant expression of biological molecules (e.g., proteins) often yields few (or no) molecules that are correctly folded and/or processed such they are able to be easily purified and/or have biological function. It would be useful to readily detect/measure correctly folded and/or processed biological molecules to optimize the production of that molecule. Moreover, often the active form of a biological molecule is not readily measurable. For example, many biological molecules, such as peptide hormones, exist in an inactive precursor form as well as an active mature form. It would be useful to be readily detect/measure the active form of a biological molecule.

Accordingly, in some embodiments, the invention provides methods and systems for rapidly identifying correctly folded and/or processed biological molecules. The invention, in some embodiments, enables selection of engineered constructs and/or engineered cells that produce correctly folded biological molecules. In some embodiments, the invention also enables the rapid detection/measurement of a mature active biological molecule.

In a first aspect, the invention provides a method for detecting the quality of a biological molecule comprising forming a first mixture of ingredients comprising: (i) a first binding agent that specifically binds to a tag, wherein the first binding agent is attached to a solid support; (ii) a decoy comprising a first portion comprising the tag attached to a second portion comprising an anchor; (iii) a sensor attached to a second binding agent that specifically binds to the anchor; and (iv) a sample suspected of containing a high quality biological molecule comprising a tag, wherein the tag of the high quality biological molecule is accessible; allowing interaction of the ingredients such that the sensor provides an output signal; and comparing the output signal to a control output signal provided by mixing and allowing interaction of a second mixture ingredients comprising the first binding agent, the decoy, and the sensor, wherein the second mixture does not comprise the sample, wherein a change in the output signal as compared to the control output signal indicates that a high quality biological molecule is present in the sample. In some embodiments, the change is a decrease as compared to the control output signal. In some embodiments, the change is an increase as compared to the control output signal.

In another aspect, the invention provides a method for detecting a high quality biological molecule in a sample, comprising: forming a first mixture of ingredients comprising: (i) a decoy comprising a first portion comprising a tag attached to second portion comprising an anchor, wherein the second portion of the decoy is attached to a solid support; (ii) a first binding agent that specifically binds to the tag, wherein the first binding agent is attached to the target to form a bridger molecule; (iii) a sensor attached to second binding agent that specifically binds to the target of the bridger molecule; and (iv) a sample suspected of containing a high quality biological molecule comprising the tag, wherein the tag of the high quality biological molecule is accessible; allowing interaction of the sensor, the decoy, the bridger molecule, and the sample such that the sensor provides an output signal; and comparing the output signal to a control output signal provided by forming a mixture of and allowing interaction of the sensor, the decoy, and the bridger molecule, wherein the second mixture does not comprise the sample, wherein a change in the output signal as compared to the control output signal indicates that a high quality biological molecule is present in the sample. In some embodiments, the change is an increase as compared to the control output signal.

In yet another aspect, the invention provides a method for detecting a high quality biological molecule in a sample, comprising: (a) forming a competitive assay formation having an output signal, comprising the steps of: (i) providing a first binding agent that specifically binds to a tag, wherein the first binding agent is attached to a solid support; (ii) providing a decoy comprising a first portion comprising the tag attached to a second portion comprising an anchor; (iii) providing a sample suspected of containing a high quality biological molecule comprising a tag, wherein the tag of the high quality biological molecule is accessible (iv) providing a sensor attached to second binding agent that specifically binds to the anchor; and (v) allowing interaction of the first binding agent, the decoy, the sensor, and the sample such that the sensor provides an output signal; and (b) comparing the output signal to a control output signal provided by interacting the first binding agent, the decoy, and the sensor without the sample, wherein a change in the output signal as compared to the control output signal indicates that a high quality biological molecule is present in the sample. In some embodiments, the sold support is a magnetic particle. In some embodiments, the change is a decrease as compared to the control output signal. In some embodiments, the change is an increase as compared to the control output signal.

In another aspect, the invention provides a method for detecting a high quality biological molecule in a sample, comprising: (a) forming a competitive assay formation having a output signal, comprising the steps of: (i) providing a decoy, the decoy comprising a first portion comprising a tag attached to second portion comprising an anchor, wherein the second portion of the decoy is attached to a solid support; (ii) providing a bridger molecule comprising a first binding agent (that specifically binds to the tag of the decoy) attached to a target; (iii) providing a sample suspected of containing a high quality biological molecule comprising the tag, wherein the tag of the high quality biological molecule is accessible; (iv) providing a sensor attached to a second binding agent that specifically binds to the target of the bridger molecule; and (v) allowing interaction of the bridger molecule, the decoy, the sensor, and the sample such that the sensor provides an output signal; and (b) comparing the output signal to a control output signal provided by interacting the bridger molecule, the decoy, and the sensor without the sample, wherein a change in the output signal as compared to the control output signal indicates that a high quality biological molecule is present in the sample. In some embodiments, the sold support is a magnetic particle. In some embodiments, the change is a decrease as compared to the control output signal. In some embodiments, the change is an increase as compared to the control output signal.

In another aspect, the invention provides a method for determining the quality of a biological molecule comprising. The method includes (a) forming a competitive assay formation having an output signal, comprising the steps of: (i) providing a decoy, the decoy comprising a first portion comprising a tag attached to second portion comprising an anchor, wherein the second portion of the decoy is attached to a solid support; (ii) providing a bridger molecule comprising a first binding agent that specifically binds to the tag of the decoy attached to a target; (iv) providing a sensor attached to a second binding agent that specifically binds to the target of the bridger molecule; (iv) allowing interaction of the sensor, decoy, and the bridger molecule such that the sensor and the solid support are non-covalently joined to provide an output signal; (b) adding a biological molecule comprising a tag to the competitive assay formation to determine if the biological molecule is a high quality biological molecule comprising an accessible tag, wherein the tag of the biological molecule and the tag of the first portion of the decoy are the same, and (c) measuring the output signal of step (b), wherein a change in the output signal of step (b) as compared to the output signal of step (a) indicates that the biological molecule is a high quality biological molecule. In some embodiments, the solid support is a magnetic bead. In some embodiments, the change is a decrease. In some embodiments, the change is an increase.

In another aspect, the invention provides a method for determining the quality of a biological molecule comprising: (a) forming a competitive assay formation having an output signal, comprising the steps of: (i) providing a first binding agent that specifically binds to a tag, wherein the first binding agent is attached to a solid support; (ii) providing a decoy comprising a first portion comprising the tag attached to a second portion comprising an anchor; (iii) providing a sensor attached to second binding agent that specifically binds to an anchor; (iv) allowing interaction of the first binding agent, the decoy, and the sensor such that the sensor and the solid support are non-covalently joined to provide an output signal; (b) adding a biological molecule comprising a tag to the competitive assay formation to determine if the biological molecule is a high quality biological molecule comprising an accessible tag, wherein the tag of the biological molecule and the tag of the first portion of the decoy are the same, and (c) measuring the output signal of step (b), wherein a change in the output signal of step (b) as compared to the output signal of step (a), wherein a change in the output signal of the competitive formation indicates that the biological molecule is a high quality biological molecule. In some embodiments, the solid support is a magnetic bead. In some embodiments, the change is a decrease. In some embodiments, the change is an increase.

In various embodiments, the method further comprises determining a quantity of the high quality biological molecule, comprising: diluting the amount of the sample comprising the high quality biological molecule added to the competitive assay formation and calibrating the output signals to determine the quantity of the high quality biological molecule present.

In yet another aspect, the invention provides a method for detecting a high quality biological molecule in a sample, the method comprising: (a) introducing a fluid comprising a plurality of magnetic particles, a decoy comprising a tag and an anchor, and a sample suspected of containing a high quality biological molecule comprising the tag, wherein the tag of the high quality biological molecule is accessible, into a fluid chamber, said magnetic particles being coated with a first binding agent that specifically binds to the tag, wherein at least one surface of the fluid chamber comprises a flexural plate wave device capable of emitting an output signal, wherein the flexural plate wave device has a membrane that is capable of vibrating, and wherein a second binding agent that specifically binds to the anchor of the decoy is attached to the membrane; (b) applying a retractable source of magnetic flux positioned external to the fluid chamber close to the membrane to create a significant magnetic field gradient to attract at least one of the plurality of magnetic particles in the fluid toward the membrane; (c) flowing a solution through the fluid chamber to remove magnetic particles not specifically bound to the membrane by the second binding agent (e.g., before, at the same time as, and/or after removing the retractable source of magnetic flux); (d) obtaining an output signal by said flexural plate wave device that corresponds to a number of the magnetic particles specifically bound to the membrane; and (e) comparing the output signal to a control output signal obtained by performing steps (a)-(d) in the absence of the sample suspected of containing the high quality biological molecule; wherein a change in the output signal as compared to the control output signal indicates that a high quality biological molecule is present in the sample. In some embodiments, the change is a decrease as compared to the control output signal. In some embodiments, the change is an increase as compared to the control output signal.

In yet another aspect, the invention provides a method for detecting a high quality biological molecule in a sample, the method comprising: (a) introducing a fluid comprising a plurality of magnetic particles, and a sample suspected of containing a high quality biological molecule comprising a tag, wherein the tag of the high quality biological molecule is accessible, and a bridger molecule comprising a target attached to a first binding agent that specifically binds to the tag into a fluid chamber, each of said magnetic particles being attached to an anchor on a decoy, the decoy comprising the anchor and the tag, wherein at least one surface of the fluid chamber comprises a flexural plate wave device capable of emitting an output signal, wherein the flexural plate wave device has a membrane that is capable of vibrating, and wherein a second binding agent that specifically binds to the target of the bridger molecule is attached to the membrane; (b) applying a retractable source of magnetic flux positioned external to the fluid chamber close to the membrane to create a significant magnetic field gradient to attract at least one of the plurality of magnetic particles in the fluid toward the membrane; (c) flowing a solution through the fluid chamber to remove magnetic particles not specifically bound to the membrane by the second binding agent (e.g., before, at the same time as, and/or after removing the retractable source of magnetic flux); (d) obtaining an output signal by said flexural plate wave device that corresponds to a number of the magnetic particles specifically bound to the membrane; and (e) comparing the output signal to a control output signal obtained by performing steps (a)-(d) in the absence of the sample suspected of containing the high quality biological molecule; wherein a change in the output signal as compared to the control output signal indicates that a high quality biological molecule is present in the sample. In some embodiments, the change is a decrease as compared to the control output signal. In some embodiments, the change is an increase as compared to the control output signal.

In various embodiments, the method further comprises determining a quantity of the high quality biological molecule, the method further comprising: (i) diluting the amount of the sample introduced into the fluid chamber in step (e) and (j) calibrating the output signals to determine the quantity of the high quality biological molecule present.

In various embodiments, the high quality biological molecule comprising the accessible tag is biologically functional.

In various embodiments, the biological molecule is a protein, a lipid, or a carbohydrate.

In various embodiments, the biological molecule comprising the tag is expressed by a cultured cell (e.g., a prokaryotic cell such as E. coli or a eukaryotic cell). In some embodiments, the cell is an insect cell (e.g., an SF9 cell). In some embodiments, the cell is a yeast cell. In some embodiments, the cell is a mammalian cell such as a COS cell, a CHO cell, a HeLa cell, a Jurkat cell, a Daudi cell, a 293 cell, an SP2/0 cell, a HT-1080 cell, an NSO cell, or a PER.C6 cell. These cells are commercially available (from, for example, the American Type Culture Collection or ATCC, Manassas, Va.).

In various embodiments, the tag is a His tag, a GST tag, a FLAG tag, a V5 tag, a myc tag, or an HA tag.

In various embodiments, the biological molecule is a secreted molecule, a cytosolic molecule or a transmembrane molecule.

In various embodiments, the decoy is a zymogen of a mature protein, wherein the tag of the first portion of the zymogen is the mature protein. In various embodiments, the mature protein is a peptide hormone. For example, the peptide hormone may be oxytocin, prolactin, vasopressin, somatostatin, insulin, or adrenocorticotropic hormone. In various embodiments, the mature protein may be a member of a complement cascade. For example, the member of the complement cascade may be a C1r protein, a C4b protein, a C2b protein, a C5a protein, or a C5b protein. In various embodiments, the mature protein may be a member of a coagulation cascade. For example, the member of the coagulation cascade is selected from the group consisting of a factor XIIa protein, a factor XIa protein, an IXa protein, a Xa protein, a thrombin protein, a fibrin protein, or factor XIII protein. In some embodiments, the mature protein is a caspase family member. For example, the caspase family member may be caspase 5, caspase 7, caspase 9, or caspase 2. In some embodiments, the mature protein is a digestive protein such as trypsin, chymotrypsin, or pepsin.

In various embodiments, the methods of the invention are carried out using AMMP technology. In various embodiments, the methods are carried out using a ViBE instrument.

BRIEF DESCRIPTION OF THE DRAWINGS

FIG. 5 is a schematic diagram showing a non-limiting embodiment of a competitive assay formation and indicating the conformation of a high quality biological molecule that can disrupt the competitive assay formation (leading to a positive result) as well as the conformation of a an incorrectly folded biological molecule (i.e., having an obstructed tag) that does not disrupt the competitive assay formation (leading to a negative result).

FIGS. 7A and 7B are a schematic diagram and a line graph, respectively. FIG. 7A shows the configuration of a non-limiting embodiment of a competitive assay formation with a non-disrupting (i.e., negative) biological molecule that is not a high quality biological molecule (i.e., it is incorrectly folded such that its His tag is inaccessible). FIG. 7B shows the results obtained from a incorrectly folded biological molecule that does not disrupt the competitive assay formation.

DETAILED DESCRIPTION OF THE PREFERRED EMBODIMENTS

Figure 1:
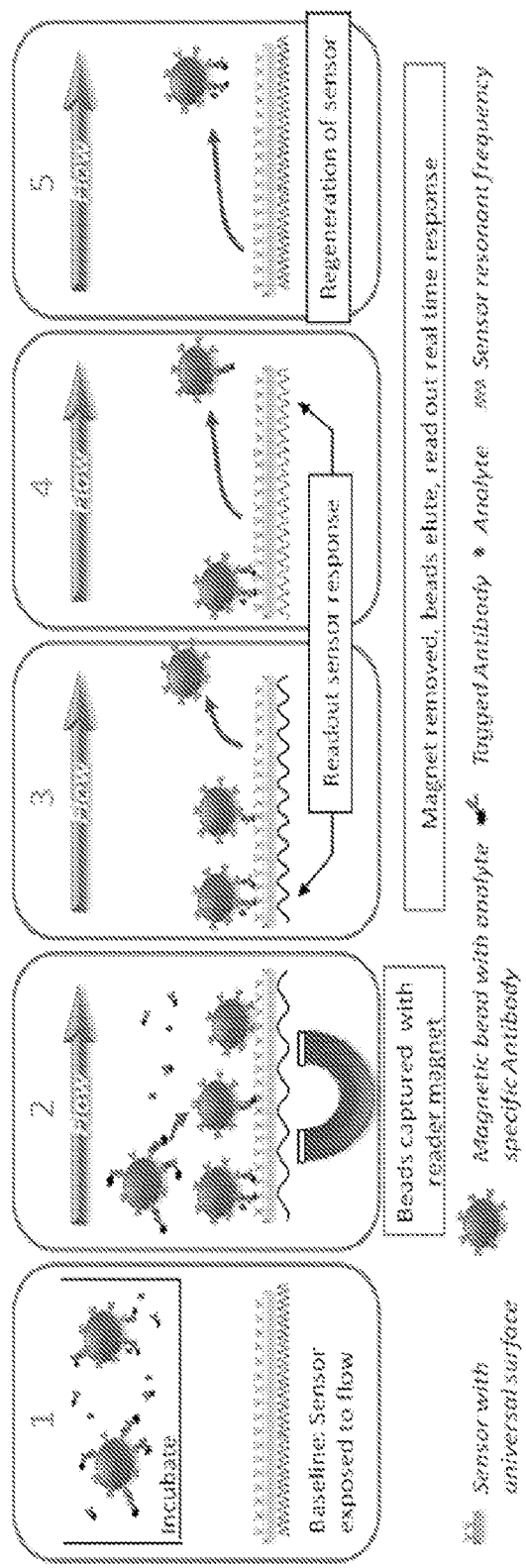
FIG. 1 is a schematic diagram showing the assay process using the AMMP technology modified to detect and/or measure the amount of a high quality biological molecule.

The present invention is based upon the development of methods and systems for accurately and consistently measuring the quantity and quality of biological molecules.

The published patents, patent applications, websites, company names, and scientific literature referred to herein establish the knowledge that is available to those with skill in the art and are hereby incorporated by reference in their entirety to the same extent as if each was specifically and individually indicated to be incorporated by reference. Any conflict between any reference cited herein and the specific teachings of this specification shall be resolved in favor of the latter.

As used herein, the following terms have the meanings indicated. As used in this specification, the singular forms "a," "an" and "the" specifically also encompass the plural forms of the terms to which they refer, unless the content clearly dictates otherwise. The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of recombinant DNA technology and immunology include Ausubel et al., Current Protocols in Molecular Biology, Wiley InterScience, New York, N.Y., (2007, and updates up to and including June 2011), Coligan et al., *Current Protocols in Immunology*, Wiley InterScience, New York, N.Y., (2007, and updates up to and including June 2011), Lo et al., *Antibody Engineering: Methods and Protocols*, Humana Press, 2003; Sambrook et al., *Molecular Cloning: A Laboratory Manual*, 2nd Ed., Cold Spring Harbor Laboratory Press, New York (1989); Kaufman et al., Eds., *Handbook of Molecular and Cellular Methods in Biology in Medicine*, CRC Press, Boca Raton (1995).

Expression of recombinant proteins is a well-known and frequently utilized technique in many fields of biology. For example, one of the first steps in transitioning into the field of proteomics is the expression and purification of the proteins encoded by the novel transcripts uncovered by high-throughput genomic studies. To accelerate this process, many expression laboratories rely on the generation of chimeric fusion proteins, in which the novel transcript is encoded with one or more specific tags, in order to simplify the operations necessary to purify the targeted protein. However, as described herein, generation of recombinant expression constructs and cells engineered to contain (and express) such constructs does not always result in a correctly folded biological molecule. For example, some of the constructs and cells, such as those described herein that are HIS tagged proteins, produce the proteins where the His tag is occluded, constricted, or otherwise obstructed. This occlusion not only prevents efficient purification of the protein using this His tag, but it also may result in an incorrectly folded protein that is not biologically functional. As used herein, by "biologically functional" is meant that a recombinant biological molecule has the same biological activity as the native biological molecule. For example, a recombinant antibody that specifically binds antigen X should be able to specifically bind to antigen X if the native antibody specifically bound antigen X. Likewise, a recombinant lck kinase should be able to phosphorylate the same substrate as a native lck kinase (i.e., an lck kinase expressed by a T cell that has not been genetically engineered in any way (e.g., a T cell into which has not been introduced by artifice any foreign nucleic acid)).

Having to purify the outputs of many expression systems under varying conditions can be highly labor intensive and time consuming in the early stages of cell line selection.

In some embodiments, the methods of the invention provide a sensitive, simple, readily useable, upstream (in crude cell lysates) method for accurate determination of correctly folded biological molecules. These molecules are referred to as high quality biological molecules.

As used herein, by "high quality biological molecule" or "high quality protein" is meant that the tag on the indicated recombinant protein or biological molecule is accessible such that the tag can be specifically bound by a binding agent that specifically binds the tag. In other words, a biological molecule that contains a tag, but contains a tag in such a way that the tag cannot be specifically bound by its specific binding agent is not a high quality biological molecule. A high quality biological molecule is folded such that its conformation allows its tag to be accessible for binding by a tag-specific binding agent.

In some embodiments, the high quality biological molecule (e.g., a high quality protein) is biologically functional. Confirmation that a biological molecule having an accessible tag can be performed by a variety of art known methods. For example, for cytosolic and transmembrane biological molecules with enzymatic activity (e.g., kinase activity), can be assessed using an in vitro assay such as an in vitro kinase activity. Biological function may also be assessed by the ability of the biological molecule to bind its partner or ligand. For example, if the native protein is a receptor for a ligand, a binding assay can be set up to confirm that the recombinant biological molecule with the accessible tag also binds the ligand.

It should be noted that a biological molecule can be any type of molecule including, without limitation, a protein, a carbohydrate, a peptide, a fatty acid, a lipid, or a nucleic acid molecule. In some embodiments, the biological molecule is a protein. Note that a protein may be modified; for example, a glycoprotein is considered to be a protein.

In some embodiments, the biological molecule is cytosolic, meaning that it stays within the cytoplasm of the cell that expressed it. In some embodiments, the biological molecule is a transmembrane molecule, meaning at least a portion of the molecule lies within the cell membrane of the cell that expressed it. In some embodiments, the biological molecule is a secreted molecule, meaning that the cell that expressed it secretes it outside of the cell into the culture media (if the cell is a cultured cell).

By "tag" (also called "hapten tag" or "hapten") is meant peptide, sugar, or fatty acid label that may be covalently or non-covalently attached to a larger biological molecule, where the tag itself may be specifically bound by a binding agent.

A tag may be noncovalently attached to a target of interest by, for example, attaching a tag (e.g., by a covalent bond) to a binding agent that specifically binds to the target. In some embodiments, the tagged binding agent will bind to the target of interest if that target is a high quality biological molecule. Upon specific binding of the tagged binding agent to the target of interest, that target becomes a tagged target.

In some embodiments, the tag is covalently attached to the target. For example, if the biological molecule is a protein and the tag is a peptide tag, the biological molecule can be covalently attached to the tag by simply engineering nucleic acid encoding biological molecule to include nucleic acid sequences that encode the tag such that the resulting fusion protein is protein attached to the tag via a peptide bond. This type of tagging using recombinant DNA methods followed by expression of the recombinant protein in cultured cells is well known. In another example, the tag (e.g., a HIS tag) may be attached to the N or C terminus of a recombinant protein via a peptide bond by, for example, attaching a nucleic acid sequence encoding a HIS tag to the 5' or 3' end of a nucleic acid sequence encoding the target of interest, and then expressing that tagged protein in a transfected or transformed cell.

Generally, if a recombinant protein is a tagged molecule, the tag is smaller than a protein (which protein is the recombinant form of the native protein). For example, a His tag is only about six amino acids long, but may be covalently attached (e.g., via a peptide bond) to a protein that is over 100 amino acids in length. In the methods described here, the binding agents that specifically bind to a tagged protein may specifically bind to either the protein portion of the tagged protein or may specifically bind to the tag portion of the tagged protein.

In some embodiments, the histidine tag (i.e., a His tag) is used to tag recombinant proteins. As used herein, a His tag (i.e., a HIS tag or polyhistidine tag) is an amino acid motif in a biological molecule (e.g., a protein) that consists of at least five histidine (His) residues (see U.S. Pat. No. 4,569, 794). The His tag is often engineered to appear at the N- or C-terminus of the protein (e.g., by adding nucleotide encoding the five or more tandem histidine residues to the 5' or 3' end of the nucleic acid sequence encoding the recombinant protein). A His tag may also be referred to as hexa histidine-tag, 6xHis-tag, and by the trademarked name HIS TAG (registered by Merck KGAA). The His tag (and, by extension, His-tagged proteins) can be purified using antibodies that specifically bind to the His tag. Additionally, the His tag is specifically bound by metals including ($Ni^{2+}$, $Co^{2+}$, and $Zn^{2+}$. When these metal ions are immobilized, the His tag (and His tagged proteins) can be readily purified. Various purification kits for histidine-tagged proteins are available from Qiagen (Valencia, Calif.), Sigma (St. Louis, Mo.), Thermo Scientific, GE Healthcare (Piscataway, N.J.), Macherey-Nagel, Clontech Laboratories (Mountain View, Calif.), and others.

In addition to the His tag examples described here, other tags or haptens include, without limitation, the GST tag (i.e., the glutathione S-transferase tag) using, e.g., the GST tag vectors (e.g., the GEX vectors) sold by GE Healthcare (Piscataway, N.J.), as catalog nos. 28-9546-56, 28-9546-53, 28-9545059, etc., see also Kaelin, W. G. et al., *Cell* 70:351, 1992 and U.S. Pat. No. 5,654,176); the FLAG tag (i.e., a tag having the sequence N'term-DYKDDDDK-C'term) using, for example, the FLAG-tag vectors sold by Sigma-Aldrich (St. Louis, Mo.) as catalog no. #E4026, #E4151, #E4776, #E4901; the V5 tag (e.g., using the V5 tag vector sold by Life Technologies (Carlsbad, Calif.) as catalog no. K4800-

01); the myc tag (e.g., using the myc-tag vectors sold by Clontech Laboratories (Mountain View, Calif.; a Takara Bio company) as catalog no. #631604, #631991); the HA tag (i.e., human influenza hemagglutinin tag having the sequence YPYDVPDYA), using, for example, the HA tag vectors sold by Clontech Laboratories as catalog no. 631992. Other binding pairs can also be used, where each of the members of the binding pair can be used as the tag. These pairs including (a) the biotin and avidin (or streptavidin) which specifically bind to each other, and (b) the strep-tag and strep-tactin, which specifically bind to each other (see, e.g., Schmidt and Skerra, Nature Protocols 2: 1528-1535, 2007; Skerra and Schmidt, *Methods Enzymol* 326: 271-304, 2000; U.S. Pat. No. 5,506,121). Vectors for attaching two tags to a single protein are also commercially available (see, e.g., the myc-His vector sold by Invitrogen (Carlsbad, Calif.); catalog no. V863-20).

In some embodiments, the ability of the tag to be specifically bound by a binding agent may aid in the purification of a tagged protein. For example, a GST tag will be specifically bound by a glutathione. Thus, solid supports coated with glutathione, which are commercially available, may be used in some of the methods described herein, and also to purify high quality biological molecules from cell culture media (for secreted recombinant tagged biological molecules that are secreted into the media that the cells are cultured in) or from cell lysates (for cytosolic or transmembrane recombinant tagged biological molecules) of cells transfected or otherwise engineered (e.g., infected with recombinant virus, transformed, etc.) to contain a recombinant vector encoding a GST-tagged biological molecule. Of course, the engineered cell may be identified as expressing a high quality biological molecule using some of the methods described herein. Glutathione coated solid supports are commercially available (e.g., Glutathione agarose and glutathione magnetic beads are available from Thermo Scientific (Watham, Mass.), catalog nos. 15160 and 88822, respectively). Other companies also sell glutathione coated solid supports (e.g., Qiagen (Valencia, Calif.), SigmaAldrich, etc.).

Other tags are specifically bounds by binding agents. For example, His tag can be specifically bound by Ni-NTA (e.g., Ni-NTA magnetic beads can be used to specifically bind His tagged biological molecules). Likewise, the V5 tag (i.e., derived from the Pk epitope present on P and V proteins of the paramyxovirus of simian virus 5 and having the sequence of 14 amino acids (GKPIPNPLLGLDST), or a shorter 9 amino acid sequence (IPNPLLGLD)) can be specifically bound by an anti-V5 tag antibody (i.e., an antibody that specifically binds to V5). Such a V5-specific antibody is sold as catalog no. ab9137 by Abcam, Cambridge, Mass. Similarly, the FLAG tag (having a sequence of DYKDDDDK) can be specifically bound by anti-FLAG tag antibodies such as the DYKDDDDK Tag Antibody sold by Cell Signaling Technology Inc. (Danvers, Mass.) as catalog no. 2368). Similarly, the HA tag (having a sequence of YPYDVPDYA) can be specifically bound by anti-HA tag antibodies, such as the anti-HA antibody sold by EMD Millipore (Billerica, Mass.) as catalog no. 05-904). Similarly, the myc tag (having the sequence of EQKLISEEDL) can be specifically bound by the anti-myc tag antibodies, such as the anti-myc tag antibodies sold by EMD Millipore as catalog nos. 05-419, 05-724, etc.

Accordingly, in one aspect, the invention provides a method for detecting the quality of a biological molecule comprising forming a first mixture of ingredients comprising: (i) a first binding agent that specifically binds to a tag, wherein the first binding agent is attached to a solid support; (ii) a decoy comprising a first portion comprising the tag attached to a second portion comprising an anchor; (iii) a sensor attached to a second binding agent that specifically binds to the anchor; and (iv) a sample suspected of containing a high quality biological molecule comprising a tag, wherein the tag of the high quality biological molecule is accessible; allowing interaction of the ingredients such that the sensor provides an output signal; and comparing the output signal to a control output signal provided by forming a mixture of and allowing interaction of a second mixture of ingredients comprising the first binding agent, the decoy, and the sensor, wherein the second mixture does not comprise the sample, wherein a change in the output signal as compared to the control output signal indicates that a high quality biological molecule is present in the sample. In some embodiments, the change is a decrease as compared to the control output signal. In some embodiments, the change is an increase as compared to the control output signal.

In another aspect, the invention provides a method for detecting a high quality biological molecule in a sample, comprising: forming a first mixture of ingredients comprising: (i) a decoy comprising a first portion comprising a tag attached to second portion comprising an anchor, wherein the second portion of the decoy is attached to a solid support; (ii) a first binding agent that specifically binds to the tag, wherein the first binding agent is attached to the target to form a bridger molecule; (iii) a sensor attached to second binding agent that specifically binds to the target of the bridger molecule; and (iv) a sample suspected of containing a high quality biological molecule comprising the tag, wherein the tag of the high quality biological molecule is accessible; allowing interaction of the sensor, the decoy, the bridger molecule, and the sample such that the sensor provides an output signal; and comparing the output signal to a control output signal provided by forming a mixture of and allowing interaction of the sensor, the decoy, and the bridger molecule, wherein the second mixture does not comprise the sample, wherein a change in the output signal as compared to the control output signal indicates that a high quality biological molecule is present in the sample. In some embodiments, the change is an increase as compared to the control output signal.

In yet another aspect, the invention provides a method for detecting a high quality biological molecule in a sample, comprising: (a) forming a competitive assay formation having an output signal, comprising the steps of: (i) providing a first binding agent that specifically binds to a tag, wherein the first binding agent is attached to a solid support; (ii) providing a decoy comprising a first portion comprising the tag attached to a second portion comprising an anchor; (iii) providing a sample suspected of containing a high quality biological molecule comprising a tag, wherein the tag of the high quality biological molecule is accessible (iv) providing a sensor attached to second binding agent that specifically binds to the anchor; and (v) allowing interaction of the first binding agent, the decoy, the sensor, and the sample such that the sensor provides an output signal; and (b) comparing the output signal to a control output signal provided by interacting the first binding agent, the decoy, and the sensor without the sample, wherein a change in the output signal as compared to the control output signal indicates that a high quality biological molecule is present in the sample. In some embodiments, the sold support is a magnetic particle. In some embodiments, the change is a decrease as compared to the control output signal. In some embodiments, the change is an increase as compared to the control output signal.

In another aspect, the invention provides a method for detecting a high quality biological molecule in a sample, comprising: (a) forming a competitive assay formation having a output signal, comprising the steps of: (i) providing a decoy, the decoy comprising a first portion comprising a tag attached to second portion comprising an anchor, wherein the second portion of the decoy is attached to a solid support; (ii) providing a bridger molecule comprising a first binding agent (that specifically binds to the tag of the decoy) attached to a target; (iii) providing a sample suspected of containing a high quality biological molecule comprising the tag, wherein the tag of the high quality biological molecule is accessible; (iv) providing a sensor attached to a second binding agent that specifically binds to the target of the bridger molecule; and (v) allowing interaction of the bridger molecule, the decoy, the sensor, and the sample such that the sensor provides an output signal; and (b) comparing the output signal to a control output signal provided by interacting the bridger molecule, the decoy, and the sensor without the sample, wherein a change in the output signal as compared to the control output signal indicates that a high quality biological molecule is present in the sample. In some embodiments, the sold support is a magnetic particle. In some embodiments, the change is a decrease as compared to the control output signal. In some embodiments, the change is an increase as compared to the control output signal.

In another aspect, the invention provides a method for determining the quality of a biological molecule comprising. The method includes (a) forming a competitive assay formation having an output signal, comprising the steps of: (i) providing a decoy, the decoy comprising a first portion comprising a tag attached to second portion comprising an anchor, wherein the second portion of the decoy is attached to a solid support; (ii) providing a bridger molecule comprising a first binding agent that specifically binds to the tag of the decoy attached to a target; (iv) providing a sensor attached to a second binding agent that specifically binds to the target of the bridger molecule; (iv) allowing interaction of the sensor, decoy, and the bridger molecule such that the sensor and the solid support are non-covalently joined to provide an output signal; (b) adding a biological molecule comprising a tag to the competitive assay formation to determine if the biological molecule is a high quality biological molecule comprising an accessible tag, wherein the tag of the biological molecule and the tag of the first portion of the decoy are the same, and (c) measuring the output signal of step (b), wherein a change in the output signal of step (b) as compared to the output signal of step (a) indicates that the biological molecule is a high quality biological molecule. In some embodiments, the solid support is a magnetic bead. In some embodiments, the change is a decrease. In some embodiments, the change is an increase.

In another aspect, the invention provides a method for determining the quality of a biological molecule comprising: (a) forming a competitive assay formation having an output signal, comprising the steps of: (i) providing a first binding agent that specifically binds to a tag, wherein the first binding agent is attached to a solid support; (ii) providing a decoy comprising a first portion comprising the tag attached to a second portion comprising an anchor; (iii) providing a sensor attached to second binding agent that specifically binds to an anchor; (iv) allowing interaction of the first binding agent, the decoy, and the sensor such that the sensor and the solid support are non-covalently joined to provide an output signal; (b) adding a biological molecule comprising a tag to the competitive assay formation to determine if the biological molecule is a high quality biological molecule comprising an accessible tag, wherein the tag of the biological molecule and the tag of the first portion of the decoy are the same, and (c) measuring the output signal of step (b), wherein a change in the output signal of step (b) as compared to the output signal of step (a), wherein a change in the output signal of the competitive formation indicates that the biological molecule is a high quality biological molecule. In some embodiments, the solid support is a magnetic bead. In some embodiments, the change is a decrease. In some embodiments, the change is an increase.

In various embodiments, the method further comprises determining a quantity of the high quality biological molecule, comprising: diluting the amount of sample comprising the high quality biological molecule added to the competitive assay formation and (f) calibrating the output signals to determine the quantity of the high quality biological molecule present.

In yet another aspect, the invention provides a method for detecting a high quality biological molecule in a sample, the method comprising: (a) introducing a fluid comprising a plurality of magnetic particles, a decoy comprising a tag and an anchor, and a sample suspected of containing a high quality biological molecule comprising the tag, wherein the tag of the high quality biological molecule is accessible, into a fluid chamber, said magnetic particles being coated with a first binding agent that specifically binds to the tag, wherein at least one surface of the fluid chamber comprises a flexural plate wave device capable of emitting an output signal, wherein the flexural plate wave device has a membrane that is capable of vibrating, and wherein a second binding agent that specifically binds to the anchor of the decoy is attached to the membrane; (b) applying a retractable source of magnetic flux positioned external to the fluid chamber close to the membrane to create a significant magnetic field gradient to attract at least one of the plurality of magnetic particles in the fluid toward the membrane; (c) flowing a solution through the fluid chamber to remove magnetic particles not specifically bound to the membrane by the second binding agent; (d) obtaining an output signal by said flexural plate wave device that corresponds to a number of the magnetic particles specifically bound to the membrane; and (e) comparing the output signal to a control output signal obtained by performing steps (a)-(d) in the absence of the sample suspected of containing the high quality biological molecule; wherein a change in the output signal as compared to the control output signal indicates that a high quality biological molecule is present in the sample. In some embodiments, the change is a decrease as compared to the control output signal. In some embodiments, the change is an increase as compared to the control output signal.

In yet another aspect, the invention provides a method for detecting a high quality biological molecule in a sample, the method comprising: (a) introducing a fluid comprising a plurality of magnetic particles, and a sample suspected of containing a high quality biological molecule comprising the tag, wherein the tag of the high quality biological molecule is accessible, and a bridger molecule comprising a target attached to a first binding agent that specifically binds to the tag into a fluid chamber, each of said magnetic particles being attached to an anchor on a decoy, the decoy comprising the anchor and the tag, wherein at least one surface of the fluid chamber comprises a flexural plate wave device capable of emitting an output signal, wherein the flexural plate wave device has a membrane that is capable of vibrating, and wherein a second binding agent that specifically binds to the target of the bridger molecule; (b) applying a retractable source of magnetic flux positioned external to the fluid chamber close to the membrane to create a significant magnetic field gradient to attract at least one of the plurality of magnetic particles in the fluid toward the membrane; (c) flowing a solution through the fluid chamber to remove magnetic particles not specifically bound to the membrane by the second binding agent; (d) obtaining an output signal by said flexural plate wave device that corresponds to a number of the magnetic particles specifically bound to the membrane; and (e) comparing the output signal to a control output signal obtained by performing steps (a)-(d) in the absence of the sample suspected of containing the high quality biological molecule; wherein a change in the output signal as compared to the control output signal indicates that a high quality biological molecule is present in the sample. In some embodiments, the change is a decrease as compared to the control output signal. In some embodiments, the change is an increase as compared to the control output signal.

In yet another aspect, the invention provides method for detecting a high quality biological molecule comprising a tag in a sample, the method comprising: (a) introducing a fluid comprising a plurality of magnetic particles and a decoy comprising the tag and an anchor into a fluid chamber, said magnetic particles being coated with a first binding agent that specifically binds to the tag, wherein at least one surface of the fluid chamber comprises a flexural plate wave device coated with a second binding agent that specifically binds to the anchor of the decoy, wherein the flexural plate wave device has a membrane that is capable of vibrating, and wherein the second binding agent is attached to the membrane; (b) applying a retractable source of magnetic flux positioned external to the fluid chamber close to the membrane to create a significant magnetic field gradient to attract at least one of the plurality of magnetic particles in the fluid toward the membrane; (c) flowing a solution through the fluid chamber to remove magnetic particles not specifically bound to the membrane by the second binding agent; (d) monitoring a first output signal by said flexural plate wave device, wherein the first signal output is monitored in the absence of the magnetic flux; (e) introducing a sample suspected of containing a high quality biological molecule into the fluid chamber; (f) repeating steps (b)-(c); (g) monitoring a second output signal by said flexural plate wave device, wherein the second signal output is monitored in the absence of the magnetic flux; and (h) comparing the first output signal and the second output signal, wherein a change in the second output signal indicates that the sample contained a high quality biological molecule. In some embodiments, the change is a decrease as compared to the control output signal. In some embodiments, the change is an increase as compared to the control output signal.

In yet another aspect, the invention provides a method for detecting a high quality biological molecule comprising a tag in a sample, the method comprising: (a) introducing a fluid comprising a plurality of magnetic particles and a bridger molecule comprising a target attached to a first binding agent that specifically binds to the tag into a fluid chamber, said magnetic particles being attached to an anchor on a decoy, the decoy comprising the anchor and the tag, wherein at least one surface of the fluid chamber comprises a flexural plate wave device coated with a second binding agent that specifically binds to a target, wherein the flexural plate wave device has a membrane that is capable of vibrating, and wherein the second binding agent is attached to the membrane; (b) applying a retractable source of magnetic flux positioned external to the fluid chamber close to the membrane to create a significant magnetic field gradient to attract at least one of the plurality of magnetic particles in the fluid toward the membrane; (c) flowing a solution through the fluid chamber to remove magnetic particles not specifically bound to the membrane by the second binding agent; (d) monitoring a first output signal by said flexural plate wave device, wherein the first signal output is monitored in the absence of the magnetic flux; (e) introducing a sample suspected of containing a high quality biological molecule into the fluid chamber; (f) repeating steps (b)-(c); (g) monitoring a second output signal by said flexural plate wave device, wherein the second signal output is monitored in the absence of the magnetic flux; and (h) comparing the first output signal and the second output signal, wherein a change in the second output signal indicates that the sample contained a high quality biological molecule. In some embodiments, the change is a decrease as compared to the control output signal. In some embodiments, the change is an increase as compared to the control output signal.

In various embodiments, the method further comprises determining a quantity of the high quality biological molecule, the method further comprising: (i) diluting the amount of the sample introduced into the fluid chamber in step (e) and (j) calibrating the output signals to determine the quantity of the high quality biological molecule present.

In some embodiments, the tag portion of the fusion biological molecule or of the decoy can be specifically bound by a binding agent.

As used herein, by "specifically bound" means that the indicated molecule or a portion thereof (e.g., a tag or anchor) is bound by a binding agent such as an antibody (where the binding agent is said to "specifically bind" the molecule) such that the interaction between the binding agent and its specific molecule is dependent upon the presence of a particular structure of the molecule; in other words, the binding agent is recognizing and binding to a specific structure rather than to all molecules (e.g., all other proteins) in general. A binding agent that specifically binds a particular molecule may be referred to as a binding agent that is specific for that molecule, a molecule-specific binding agent, or an anti-molecule binding agent. For example, an antibody that specifically binds to a His tag may be referred to as an anti-His antibody or a His-specific antibody. By "binding fragment" means a fragment or portion of a binding agent that specifically binds the indicated molecule. For example, the Fab fragment of an antibody is a binding fragment of an antibody. In some embodiments, a binding agent (e.g., an antibody) that specifically binds its target molecule has a dissociation constant ($K_D$) for its target molecule of $1\times10^{-6}$ M or less. In some embodiments, a binding agent that specifically binds to its target molecule binds with a $K_D$ of $1\times10^{-7}$ M or less, or a $K_D$ of $1\times10^{-8}$ M or less, or a $K_D$ of $1\times10^{-9}$ M or less, or a $K_D$ of $1\times10^{-10}$ M or less, of a $K_D$ of $1\times10^{-11}$ M or less, of a $K_D$ of $1\times10^{-12}$ M or less. In certain embodiments, a binding agent that specifically binds to its target (or tag) binds with a $K_D$ of 1 pM to 500 pM, or between 500 pM to 1 uM, or between 1 uM to 100 nM, or between 100 mM to 10 nM.

In some embodiments, the binding agent is an antibody. As used herein, the term "antibody" is meant to include intact immunoglobulin molecules of any isotype or subisotype (e.g., IgG, IgG1, IgG2a, IgG2b, IgG3, IgG4, IgM, IgD, IgE, IgE1, IgE2, or IgA) from any species (e.g., human, rodent, camelid), as well as binding fragments (also called antigen binding domain) thereof, such as Fab and Fab'; variants thereof such as scFv, Fv, Fd, dAb, bispecific scFvs, diabodies, linear antibodies (see, e.g., U.S. Pat. No. 5,641, 870, Zapata et al., Protein Eng 8 (10): 1057-1062, 1995); single-chain antibody molecules; and multispecific antibodies formed from antibody fragments; and any polypeptide comprising a binding domain which is, or is homologous to, an antigen binding domain (i.e., the portion of an antibody that retains the target-specific binding activity of the intact antibody).

Note that because the interaction of a binding agent to its specific molecule is so specific, some binding agent:molecule pairs are well known. For example, the interaction of avidin (e.g., streptavidin) and biotin is highly specific and strong. In this situation, if streptavidin is referred to as a binding agent, then biotin will be referred to as the specific molecule. And vice versa.

Any technique and/or instrument can be employed to detect the presence of and/or quantity of the high quality biological molecules as describe herein. For example, high quality biological molecules can be detected via their accessible tags using antibodies that specifically bind to the tag and antibodies that specifically bind to the target. Such techniques include standard pull-down assays (i.e., immunoprecipitation), Western blotting analyses, ELISA, SDS-PAGE, FACS scan, etc. These methods are well known (see, e.g., Ausubel et al., supra).

In some embodiments, the methods described herein that allow for the detection and measurement of tagged proteins are performed in non-reducing conditions. By "reducing conditions" is meant conditions that reduce (or break) disulfide linkages within a protein. Some techniques including SDS-PAGE electrophoresis that have been used to assess the purity and amount of recombinant proteins are performed under reducing conditions which linearize and otherwise expose a hidden tag. Of course, if a hidden tag is exposed and detected, that recombinant protein, when folded in non-reducing conditions, may not, in fact, be a high quality biological molecule. Because techniques such as SDS-PAGE and Western blotting analysis, which are typically run under reducing conditions (thus linearizing and exposing otherwise cryptic tags), these techniques have proven to be only marginally predictive of the purification yield for the native protein (i.e., a high quality protein).

One non-limiting method for detecting and/or measuring a high quality biological molecule is an immunoprecipitation assay. This assay may also be referred to as a pull down assay. Generally, a first binding agent (e.g., a target-specific antibody) is attached to a solid support (e.g., an agarose bead). That bead-coated antibody is incubated with a sample suspected of containing a high quality biological molecule such that that a complex will form between the bead and the target (which may be a high quality biological molecule). The mixture is allowed to precipitate (e.g., using gravity or centrifugation), and the beads will "pull down" any molecules specifically bound to them by the antibodies coating the beads. A second binding agent is added (e.g., that specifically binds to a tag), and if the pulled down target is a high quality biological molecule, the binding of that second binding agent can be detected (e.g., using a secondary antibody that is detectable. By "detectable" with respect to a molecule (e.g., a target, a tag, or a binding agent (e.g., an antibody)) means a chemical, biological, or other modification of or to the molecule to operably link that molecule to a detectable moiety. Detectable moieties include, without limitation, fluorescent labels, mass labels, dyes, and radioisotopes, by which the presence of the modified molecule may be detected.

In some embodiments, the methods for detecting and/or measuring a high quality biological molecule may utilize the acoustic membrane and microparticle (AMMP®) technology. AMMP assays are described in U.S. Pat. Nos. 7,300,631; 7,598,094; 7,611,908; and 7,615,381, 7,629,137; as well as U.S. Patent Application Publication No. 2010/023031, all of which are hereby incorporated by reference in their entirety. In one example of using the AMMP technology, which can be performed on the ViBE® instruments sold by BioScale, Inc., Lexington, Mass., magnetic solid supports (e.g., magnetic microparticles or beads) are attached (e.g., via conjugation or specific binding) to a first binding agent that specifically binds to a target of interest. A second binding agent that also specifically binds to the target of interest (e.g., at an epitope on the target that is different from the epitope specifically bound by the first binding agent) is attached to a sensor that is acoustically connected to a piezoelectrically-driven microchip. This piezoelectrically-driven microchip (called a flexural plate wave device) will respond using sensitive acoustics to the binding of molecules (e.g., target proteins attached the microparticles) to its sensor surface (i.e., a membrane on the flexural plate wave device). In the embodiment where the AMMP assay is used, a "sensor surface" or "membrane" (as used herein) is the specific surface connected to an acoustically sensitive chip in the flexural plate wave device and the "output signal" is the acoustic signal from the chip. In some embodiments, the portion of the binding agent that does not contain the binding fragment is attached to the solid support (e.g., either the sensor surface or the microparticle bead surface). For example, if the binding agent is an antibody, the portion of the antibody attached to the solid support may be, for example, the Fc portion of the antibody leaving the antigen binding domain of the antibody (i.e., the binding fragment of the antibody) free to interact with any target present in the sample.

Note that the binding agent (e.g., an antibody) may be attached to the sensor by any means. For example, if the binding agent is an antibody, the sensor may be coated with protein A, to which the Fc portion of the antibody will attach. The binding agent may also be chemically conjugated to the sensor using standard methods (see, e.g., "Thermo Scientific Pierce Crosslinking Technical Handbook" published by ThermoScientific (part of ThermoFisher Scientific), Article No 1601673, 04/09; copyright 2009 by Thermo Fisher Scientific, Inc.).

Also note that as referred to throughout, when as sensor or bead is described as being coated with a molecule (e.g., a binding agent or the anchor portion of a decoy), the word "coat" simply means that at least some of the surface of the sensor or the bead is attached to the indicated molecule. "Coating" does not, however, mean that every surface area of the sensor or bead is attached to the indicated molecule. The attachment of the indicated molecule to the sensor or bead may be through any means (e.g., covalent or non-covalent). For example, a bead can be coated with an antibody by coating (or attaching) the bead to protein A and then mixing the antibody with the protein A coated bead such that the Fc portion of the antibody will specifically bind the protein A on the bead. Similarly, the sensor can be coated (or attached) to streptavidin. Streptavidin will specifically bind with high affinity to biotinylated molecules, such as a biotinylated antibody. By mixing the biotinylated antibody with the streptavidin coated sensor under conditions where the streptavidin can interact with the biotinylated antibody, one can achieve an antibody coated sensor.

In some embodiments of the present invention, AMMP assays may be applied to protein purification of high quality biological molecules such as polyhistidine-tagged proteins.

Likewise, in some embodiments, the methods described herein can be applied to the identification and purification of high quality biological molecule such as GST tagged proteins. Such GST tagged proteins may be detected, for example, with a binding agent that specifically binds to GST microparticles (e.g., the binding agent may be a glutathione coating on the microparticles).

In some embodiments, the AMMP assays are configured to use only an antibody (anti-HIS) to attain detection and relative quantitative measurement of HIS-tagged proteins in sample. Proteins of ranging size, typically <500 kDa, are targeted in these kinds of assays. Note that by "a binding agent" (e.g., "an antibody" or even a "single antibody") is not meant as one molecule, but rather multiple molecules comprising multiple copies of a single molecule. For example, an "anti-His antibody" means multiple copies of a single antibody that specifically binds to an His tag (e.g., the antibody produced by clone HIS.H8 and sold by EMD Millipore (Billerica, Mass.) as catalog No. 05-949).

In accordance with various embodiments of the invention, a sample suspected of containing a target is incubated or mixed with the target-specific binding agent-coated magnetic beads (also called microparticles) such that if the target is present, target:bead complexes will form. These target: bead complexes are then brought into contact with the vibrating microchip-based sensor by applying a magnetic field to attract the magnetic beads to the sensor surface. Binding of the bead to the sensor via the target (i.e., the target serves as a bridge between the bead and the sensor) will cause the vibrating sensor surface to slow down. Specific binding of the beads to the sensor (i.e., the membrane of the flexural plate device) can be determined by removing the magnetic field and detecting binding of the bead by detecting a reduction in the vibration of the sensor in the absence of the magnetic field This is called an output signal and can be measured using the ViBE instrument in AMMP units.

In some embodiments, the methods for detecting and/or measuring a high quality biological molecule are performed homogenously. In the assay described herein, targets and/or fashioned competitors to targets, are captured by the beads (also referred to as microparticles) in the sample mix which is flowed over the sensors. Identification of tagged target molecules by the sensor's affinity surfaces occurs when the complexes (i.e., the microparticle: target complexes) in the sample are first attracted to the sensor by magnetic attraction of the magnetic microparticles to the sensor. This attraction occurs prior to a buffer wash. The magnetic field, thus, holds the microparticle:target complexes in situ. High sensitivity is achieved in this homogenous assay, especially in the case of low affinity binders, since the captured (i.e., specifically bound) target is not washed away, nor subject to off-rate kinetics as is the case in multistep based assays that involve separation from sample prior to detection, as is the case with most plate immobilized or spot type assays such as ELISA.

In some embodiments, the AMMP technology is modified to detect a high quality biological molecule. Accordingly, in some embodiments, the methods of the invention are performed using AMMP technology.

Since the AMMP assay uses no chemical, enzymatic or optical amplifications (compare to Zhao et al., *Anal Biochem.* 399(2):237-245, 2010), the AMMP assay can deliver sensitive and quantitative results in upstream lysates and supernatant matrices and therefore can be used pre purification for detection of the fusion protein product. AMMP assays disclosed herein are therefore used upstream in screening and optimization of the constructs used to express the desired biological molecule, that is a high quality biological molecule. This is because in about ¼ to ⅓ of the expression constructs, the tag on the expressed recombinant protein is occluded for purification and detection.

Note that by "expression construct" or "expression vector" is meant a nucleic acid vectors into which is inserted nucleic acid encoding a desired biological molecule that is positioned in the vector such that biological molecule will be expressed (i.e., transcribed and/or translated) into protein in a cell into which the vector has been introduced (e.g., by transfection or translation). The cell which has been thus manipulated to express the expression vector may be referred to as an engineered cell or a recombinant cell. The expression vector may have, for example, a promoter upstream (i.e., 5' to the start site (i.e., the first codon encoding the N'terminal amino acid)) of the inserted nucleic acid and/or may have a polyA tail downstream (i.e., 3' to the stop codon) of the inserted nucleic acid.

Common expression vectors include the pcDNA vectors from Invitrogen (a Life Technologies company, Carlsbad, Calif.); the In some embodiments, the expression vector used will insert a nucleotide sequence encoding a tag onto the 5' or 3' end of the inserted nucleic acid encoding a target of interest, resulting in a tag at the 5' or 3' end of the encoded target. Such expression vectors are commercially available. For example, the pGEX vectors (from GE Healthcare, Piscataway, N.J.) can be used to add a GST tag to a recombinant protein target. Similarly, the pSELECT-HA-tag vector and the PSELECT His-Tag vector can be purchased from InvivoGen (San Diego, Calif.) and used to generate, respectively, GST-tagged proteins and His-tagged proteins. Qiagen (Valencia, Calif.) also sells QIAgenes and pQETriSystem expression constructs that will allow expression of a His-tagged target of interested in prokaryotic, insect, and mammalian cell lines.

Constructs (and recombinant cells into which are introduced with such constructs) that encode (or, in the case of recombinant cells, express) improperly folded recombinant proteins are undesirable and are preferably excluded early in the process of construct selection to avoid time and resources being spent propagating recombinant cells that do not express a high quality molecule (e.g., because the cells were transfected with the undesirable construct or because the construct integrated into a undesirable site in the cell's genome). Recombinant cells that do not produce large quantities of a high quality biological molecule can also be quickly excluded in favor of recombinant cells that produce high quantities of a high quality biological molecule.

It should be noted that any type of cell can be used to express a biological molecule of interest. For example, prokaryotic cells such as bacteria can be used, and eukaryotic cells such as yeast cells, insect cells, and mammalian cells can be used. In some embodiments, mammalian cells are used. The American Type Culture Collection (ATCC, Manassas, Va.) sells numerous cells, any of which can be used to express the high quality biological molecules described herein. Thus, mammalian cells that can express high quality biological molecules include, without limitation, COS cells, CV1 cells, HeLa cells, CHO cells, Jurkat cells, Raji cells, Daudi cells, 293 cell, NIH-3T3 cells, SP2/0 cells, HT-1080 cells, NSO cell, and PER.C6 cells.

In some embodiments, the AMMP assay enables rapid identification of these undesirable constructs and/or recombinant cells before a particular construct and/or cell is selected for further propagation and expansion, or as part of the selection process. Similarly, in some embodiments, the method described herein allows rapid identification of a desirable construct and/or recombinant cell. Such desirable constructs and/or recombinant cells respectively encode and express a high quality biological molecule.

In some embodiments, the methods of the invention are useful for purifying high quality biological molecules. And in some embodiments, the methods of the invention determine the quantity of a high quality biological molecule by starting with a purified molecule.

As used herein, by "purified" is meant that the referenced biological molecule (e.g., a recombinant protein) is removed or separated from other components present in its natural environment. For example, a purified recombinant protein is one that is separated from other components of a eukaryotic cell (e.g., the endoplasmic reticulum or cytoplasmic proteins and RNA). A purified biological molecule may be at least 60% free, or at least 75% free, or at least 90% free, or at least 95% free from other components present in natural environment of the indicated biological molecule.

It should be noted that protein purification is a series of processes intended to isolate a single type of protein from a complex mixture. Protein purification is vital for the characterization of the function, structure and interactions of the protein of interest. The starting material is usually a biological tissue or a cell tissue culture (either prokaryotic or eukaryotic cell culture). The various steps in the purification process may free the protein from a matrix that confines it, separate the protein and non-protein parts of the mixture, and finally separate the desired protein from all other proteins. Separation of one protein from all others is typically the most laborious aspect of protein purification. Separation steps exploit differences in protein size, physicochemical properties and binding affinity.

Polyhistidine-tags are often used for affinity purification of polyhistidine-tagged recombinant proteins expressed in *Escherichia coli* (Hengen, P., *Trends Biochem Sci.* 20(7): 285-6, 1995) and other prokaryotic expression systems. Bacterial cells are harvested via centrifugation and the resulting cell pellet lysed either by physical means or by means of detergents and enzymes such as lysozyme. At this stage, the raw cell lysate contains the recombinant protein among several other proteins originating from the bacterial host. This mixture is incubated with affinity media such as Ni Sepharose, NTA-agarose, His60 Ni, HisPur resin, or TALON resin. Affinity media contain bound metal ions, either nickel or cobalt to which the polyhistidine-tag binds with micromolar affinity. The resin is then washed with phosphate buffer to remove proteins that do not specifically interact with the cobalt or nickel ion. Washing efficiency can be improved by the addition of 20 mM imidazole (proteins are usually eluted with 150-300 mM imidazole). Generally nickel based resins have higher binding capacity, while cobalt based resins offer the highest purity.

Affinity purification using a polyhistidine-tag usually results in relatively pure protein when the recombinant protein is expressed in prokaryotic organisms. Depending on downstream applications including the purification of protein complexes to study protein interactions, purification from higher organisms such as yeasts or other eukaryotes may require a tandem affinity purification using two tags to yield higher purity (see Gavin et al., *Nature* 415(6868):141-147, 2002). Alternatively, single-step purification using immobilized cobalt ions rather than nickel ions generally yields a substantial increase in purity and requires lower imidazole concentrations for elution of the his-tagged protein.

Polyhistidine-tagging is useful for purifying recombinant proteins in denaturing conditions because its mode of action is dependent only on the primary structure of proteins. Generally for this sort of a technique, histidine binding is titrated using pH instead of imidazole binding—at a high pH histidine binds to nickel or cobalt, but at low pH (a pH of approximately 6 for cobalt and a pH or approximately 4 for nickel), histidine becomes protonated and is competed off of the metal ion. In contrast, antibody purification often requires as a prerequisite the proper (native) folding of proteins involved. The methods described herein, which are useful for detecting whether or not a protein is properly folded, are useful to employ before the expansion of cells and time consuming purification processes are undertaken.

Note that where the His-tag is employed in attempts to express a high quality biological molecule, purification with a polyhistidine-tag column can retain several well known proteins as impurities. One of them is FKBP-type peptidyl prolyl isomerase, which appears around 25 kDa (SlyD). Impurities are generally eliminated using a secondary chromatographic technique, or by expressing the recombinant protein in a SlyD-deficient *E. coli* strain. Alternatively cobalt based resins do not bind SlyD from *E. coli* and can be used for a single step purification (see Hochuli et al., *Bio/Technology* 6: 1321-1325, 1988.

In some embodiments, the methods described herein for detecting and measuring recombinant proteins does not require purification of the recombinant protein prior to its identification and quantification. For example, in some previously known methods, the protein of interest must first be purified prior to its accurate measurement. In the present method, the detection, purification, and measurement of a recombinant protein can take place in a single step. Cell types including *E. coli* cells, insect cells, and mammalian cells are all capable of being used to produce the high quality recombinant proteins described herein.

FIG. 1 shows a non-limiting example of the AMMP assay being used to detect a high quality biological molecule that is tagged with an accessible tag. A known target is also tagged with the same tag as the high quality biological molecule. For example, if a his tagged biological molecule is sought to be detected in a sample, the known target is attached (e.g., via a covalent bond) to a his tag as well. Briefly, as shown in FIG. 1, the sample suspected of containing a high quality biological molecule and the tagged known target are first incubated with antibody-coated beads, where the antibodies specifically bind to the target portion of the tagged target, and also with free antibody that specifically binds to a tag which, in a high quality biological molecule, will be accessible for binding by the antibody. In step 2, the sample suspected of containing the high quality biological molecule, the tagged target, the beads and the free antibody) are passed over the sensor of the ViBE instrument and the beads are collected to the sensor surface using a magnet. The sensor surface of the ViBE instrument is coated with antibodies that will specifically bind to a region of the free antibody that does not interfere with the ability of the free antibody to specifically bind to the tag. A competitive assay formation (e.g., a sandwich) will form between the antibody on the bead, the free antibody, the tagged target, the target-specific antibody on the sensor. However, if a high quality biological molecule is present in the sample, the accessible tag on the high quality biological molecule will compete with the tagged target for binding to the free antibody. In step 3, the beads are briefly washed with a buffer while still engaged by the magnet. In step 4, under continuing flow, beads that do not specifically bind to the sensor will elute (i.e., come off) from the sensor. In steps 3 and 4, the output signal is made. Finally, in step 5, the sensor surface of the ViBE instrument is regenerated using the regeneration fluid (available from BioScale, Inc.) which removes any remaining bead and/or a competitive assay formation still bound to the sensor surface.

The amount and strength of binding gives a measurable signal with reference to total amount of tagged target exposed to the sensors. It is important to note that FIG. 1 is representative and does not show the total amount of magnetic beads per assay relative to a sensor surface. In the practice of an AMMP assay, thousands of particles are brought to each sensor surface in the process of each assay, each particle having the possibility of thousands of binding sites that could be bridged, via a bound target, to the surface of the sensor.

AMMP signal units are recorded at various time points in the wash sequence and numerically represent the fraction of beads remaining, during and post wash when the magnetic field has been removed, of the total exposed to the sensor during the sample loading period with the magnetic field.

Figure 2:
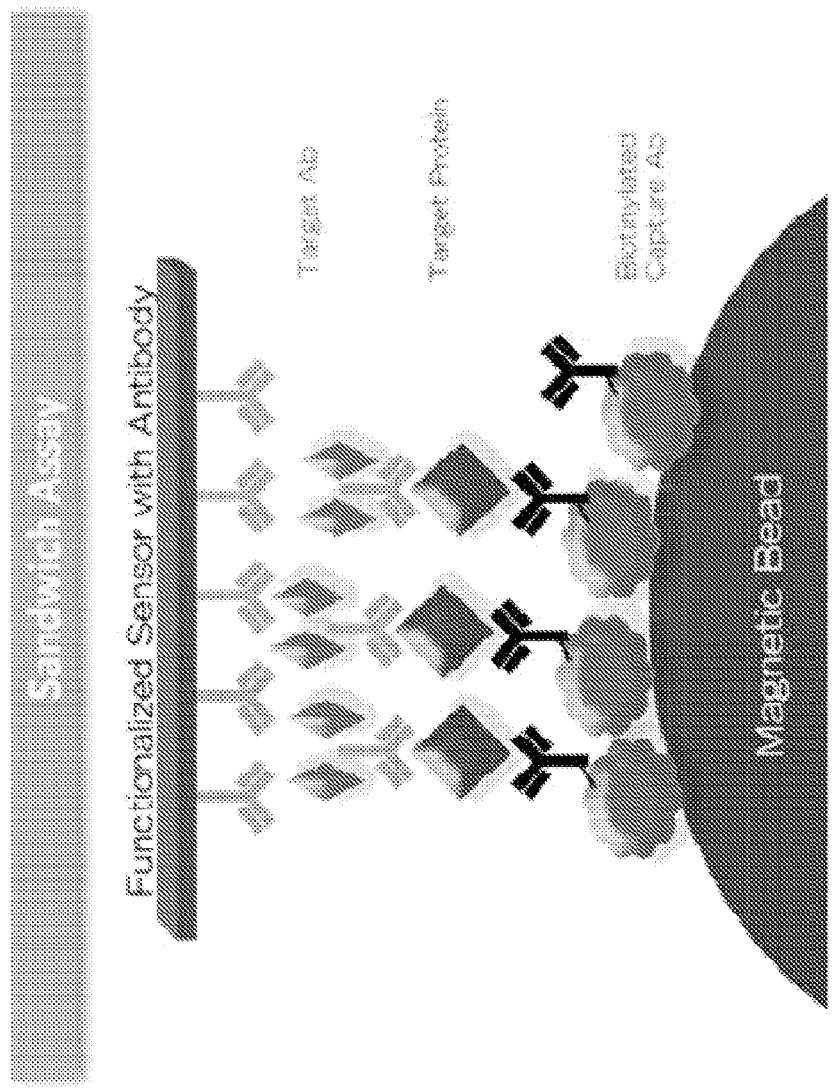
FIG. 2 is a schematic diagram showing a non-limiting embodiment of a configuration of the methods described herein. This is a non-limiting form of a competitive assay formation in the form of a sandwich assay. In this embodiment, the tag is non-covalently attached to the target. The first target-specific antibody that is coating the magnetic bead is shown in black while the tag on the second target-specific antibody is shown in green diamonds and the target (labeled "Target Protein") is shown as red squares. In this embodiment, free target or free tag will disrupt the competitive assay formation and reduce the output signal.

A non-limiting example of a junction of sensor surface bound to the magnetic bead in the process described in FIG. 1 is shown in detail in FIG. 2. In FIG. 2, the target-specific antibodies are coating onto the magnetic beads using the streptavidin:biotin interaction. Here, the Fc region of the antibodies are biotinylated and specifically bind to streptavidin-coated magnetic beads. The antigen-binding domain of the antibodies are thus free to specifically bind to the target.

In this example in FIG. 2, a known target-specific antibody that is in solution is tagged with (i.e., bound to) a generic tag (through, for example, lysine coupling). The generic tag is shown in FIG. 2 as a green diamond. Antibodies that specifically bind the tag are applied (via their Fc regions) to the sensor surface. As shown in FIG. 2, the target:antibody complexes that are formed on the magnetic beads (i.e., the microparticles) via a second antibody that specifically binds to the target are specifically bound by the sensor surfaces.

In the example of FIG. 2, a high quality biological molecule comprising an accessible tag will disrupt the competitive assay formation (i.e., the sandwich shown in FIG. 2) by the accessible tag on the high quality biological molecule. That accessible tag will disrupt the competitive assay formation by competing for binding of the anti-tag antibodies on the sensor, thereby either preventing the bead from binding to the sensor or by competing the already-bound bead off the sensor. This disruption by the high quality biological molecule will thereby change the output signal (i.e., decreasing it). Thus, in this non-limiting embodiment of the invention shown in FIG. 2, the presence of a high quality biological molecule can be detected.

Thus, the presence of a high quality biological molecule may be assessed using the method outlined in FIG. 1, for example, by determining if any target:bead complexes remain adhered to the sensor surface under flow conditions in step 4. In other words, if an output signal continues to be obtained at the same level regardless of the addition of the sample, under flow conditions, the sample must not have contained a high quality biological molecule with an accessible tag to which the antibodies coating the sensor surface can specifically bind.

In some embodiments, the methods of the invention can be employed to quantitate the amount of a high quality biological molecule in sample. This is useful, for example, when a recombinant vector encoding a tagged biological molecule (where the tag will be accessible in the high quality biological molecule) is transfected (e.g., via electroporation or DEAE-dextran) into cells, and individual cells are cloned. A single clone expressing a high quality biological molecule in high quantities is desirable, but detecting such a clone can be cumbersome and time-consuming. With the methods of the invention, cell lysates (if the molecule is an cytosolic or transmembrane molecule) or cultured supernatant (if the molecule is a secreted molecule) can be taken from individual clones and screened using the methods described herein to identify the clone that produces a high quality biological molecule in high quantities.

Accordingly, in some embodiments, the system of FIGS. 1 and 2 can be modified and calibrated with known spikes of recombinant or analyte analogues in representative sample matrix. In this manner, the amount of the high quality biological molecule present in the sample may be quantitated.

The amount of the high quality biological molecule in the sample can be obtained by using a decoy (also called a Tracer or a competitor) that will form a bridge between the sensor and the bead. This bridge, referred to as a competitive assay formation, can be disrupted (e.g., broken or prevented from being formed) by a high quality biological molecule that competes with the decoy. In some embodiments, the competitive assay formation is prevented from being formed (i.e., the bridge is not formed) in the presence of the high quality biological molecule. In some embodiments, the competitive assay formation is formed but is then broken by the high quality biological molecule.

Figure 3:
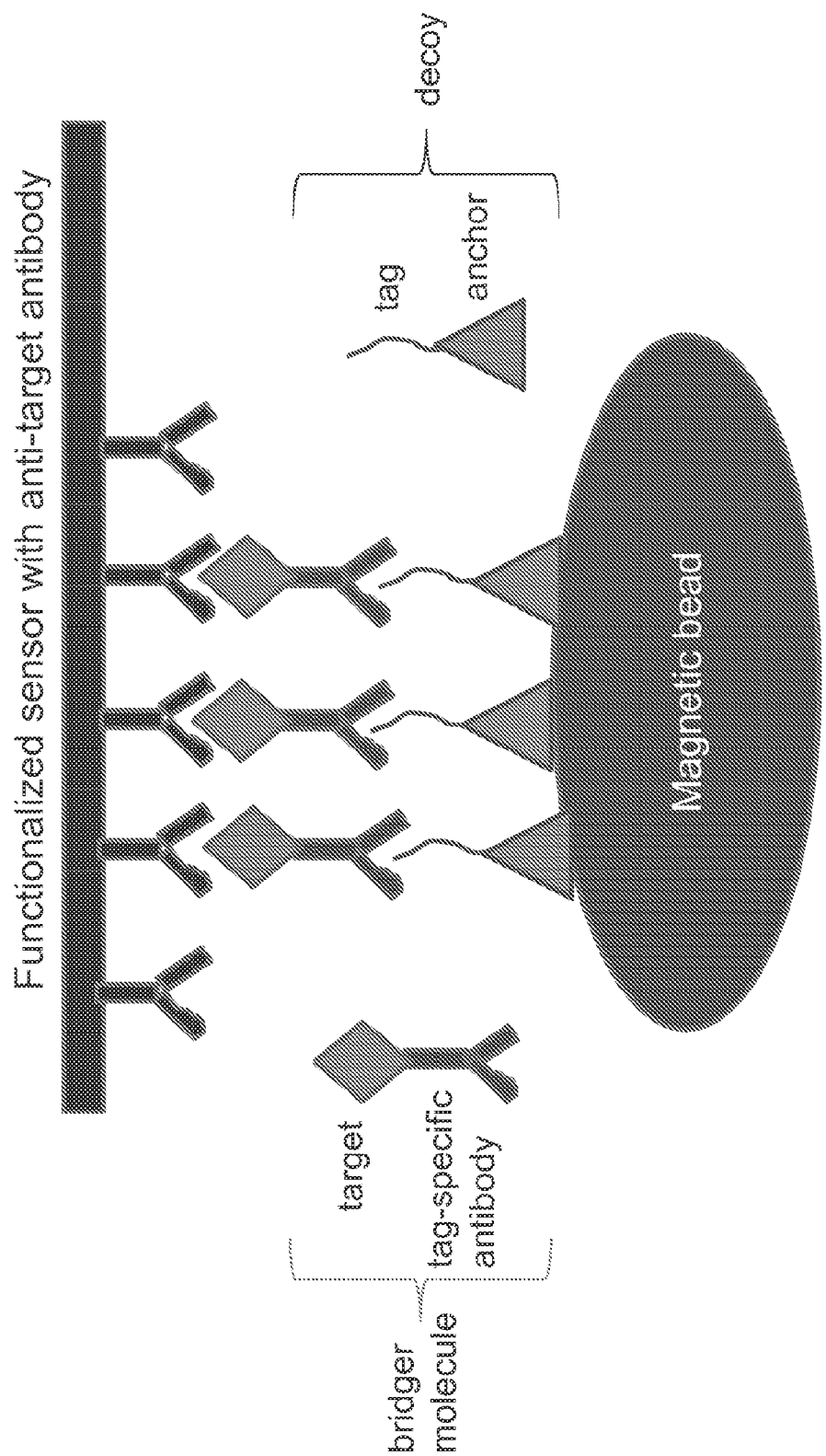
FIG. 3 is a schematic diagram showing a non-limiting example of a competitive assay formation showing the specific binding of the bead to the sensor creating a high output signal. The competitive assay formation comprises a target-specific antibody coated sensor surface, a magnetic bead coated with a decoy, where the tag portion of the decoy is free to interact with tag-specific binding agent portion of a bridger molecule that comprises a target attached to the tag-specific binding agent (in FIG. 3, this tag-specific binding agent is shown as an antibody). In this embodiment, free target or free tag (e.g., a tagged decoy protein), that may be introduced, for example, as a sample mixture with the beads with, in some embodiments, secondary reagents, will disrupt the competitive assay formation and reduce the output signal.
Figure 4:
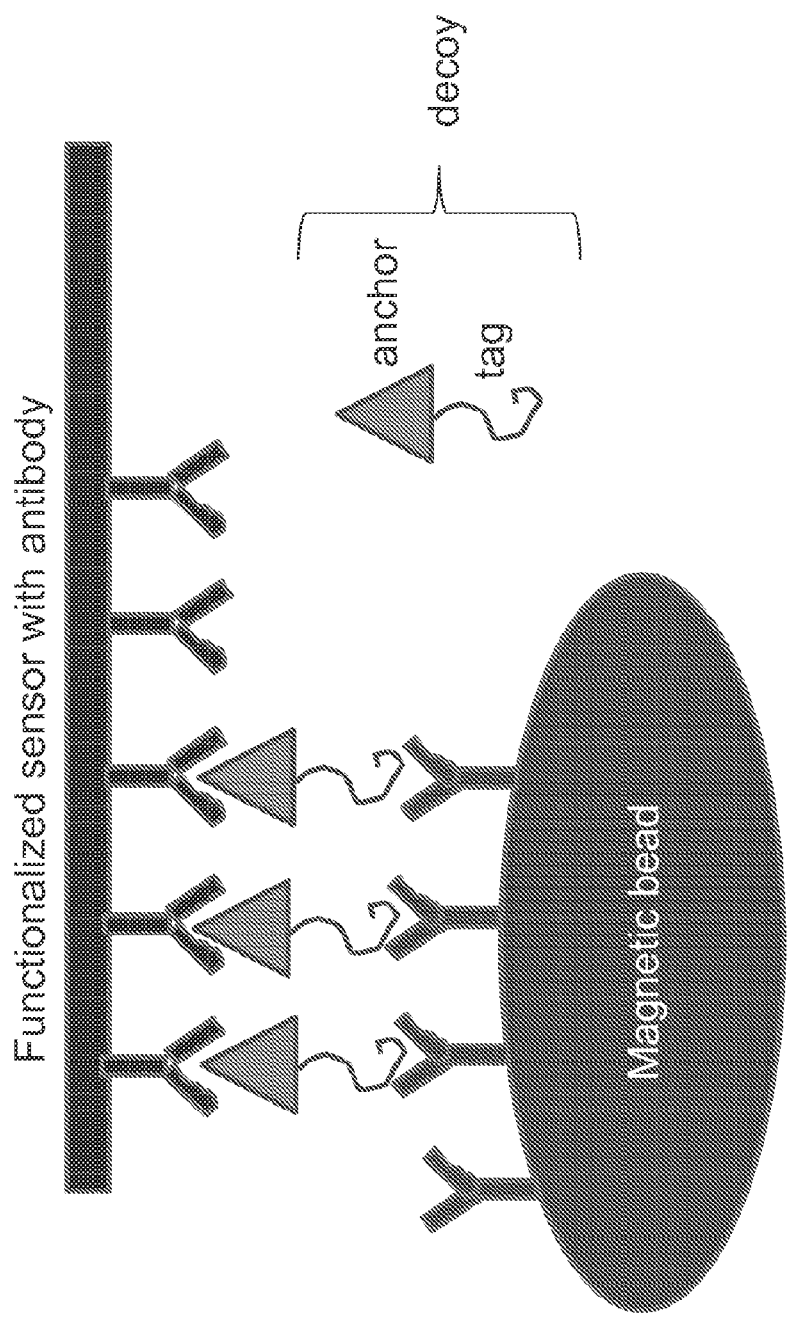
FIG. 4 is a schematic diagram showing a non-limiting example of a competitive assay formation showing the specific binding of the bead to the sensor creating a high output signal. The competitive assay formation comprises a sensor surface coated with antibodies that specifically bind to an anchor portion of the decoy, a magnetic bead coated with tag-specific antibodies, and a decoy. In this embodiment, free tag (e.g., a high quality biological molecule with an accessible tag) will disrupt the competitive assay formation and reduce the output signal.

For example, referring to FIG. 1, in step 3, the magnetic bead may be specifically bound to the sensor surface via a configuration shown in FIG. 3 or 4. These configurations may be referred to as competitive assay formations. In the non-limiting example of FIG. 3, the competitive assay formation is made by adding to the anti-target binding agent coated sensor, a mixture of ingredients comprising a bridger molecule comprising a target portion (i.e., the target to which the anti-target binding agent coating sensor will specifically bind) and an anti-tag binding agent portion, and a decoy coated magnetic bead, where the decoy comprises an anchor portion that attached to the bead and a tag portion that is free to interact with the anti-tag portion of the bridger molecule. The presence of the bridger molecule in FIG. 3 will cause the bead to specifically bind to the sensor in step 3 of the process depicted schematically in FIG. 1. Similarly, in FIG. 4, the competitive assay formation is made by adding to the anti-anchor binding agent coated sensor, a mixture of ingredients comprising a decoy comprising an anchor portion (i.e., the anchor to which the anti-anchor binding agent coating the sensor will specifically bind) and a tag portion, and an anti-tag binding agent coated magnetic bead. The presence of the decoy in FIG. 4 will cause the bead to specifically bind to the sensor in step 3 of the process depicted schematically in FIG. 1.

When sample suspected of containing a high quality biological molecule is added to a mixture forming a competitive assay formation at any step during the formation of either of these competitive assay formations under conditions where specific binding of the various binding agents to their specific targets will occur, if that sample contains is a high quality biological molecule (and thus has an accessible tag), it will disrupt the binding of the magnetic bead to the sensor in both FIG. 3 and FIG. 4 by either preventing the formation of the competitive assay formation or breaking up the competitive assay formation already formed. Note that in FIG. 3, some amount of bridger molecule unbound to the sensor may remain in the mixture resulting in the formation of the competitive assay formation. Similarly, that in FIG. 4, some amount of decoy unbound to the sensor may remain in the mixture resulting in the formation of the competitive assay formation. In these non-limiting configurations, the high quality biological molecule will reduce the output signal in step 4 of the FIG. 1 process.

Note that if a known quantity of the bridger molecule (i.e., the tag-specific binding agent attached to the target molecule) or a known quantity of free decoy (i.e., not attached to a magnetic bead) is present in FIG. 3, the amount of high quality biological molecule in the mixture (i.e., the mixture comprising the sample suspected of containing the high quality biological molecule, the decoy-coated beads, the bridger molecule, and the anti-target antibody-coated sensor) can be calculated by determining how much bridger molecule or how much free decoy was present in FIG. 3 and how much the output signal is reduced as compared to the output signal in the mixture without the sample (i.e., the mixture comprising the bridger molecule, the beads, and the sensor, but without the sample suspected of containing the high quality biological molecule). Additionally in the non-limiting configuration of FIG. 3, different amounts of the free decoy (i.e., not attached to a bead) or free bridger molecule (i.e., a molecule comprising the tag-specific binding agent attached to the target) may also be added to a mixture comprising the decoy-coated beads, the bridger molecule, and the anti-target coated-coated sensor that does not contain any sample suspected of containing a high quality biological molecule, and output signals can be recorded. These output signal measurements can be used to create a standard curve where the amount that the output signal decreases can be plotted against the amount of the added free decoy or the added bridger molecule.

This standard curve can be used as a reference. In one non-limiting embodiment of the non-limiting configuration of FIG. 3, when a sample suspected of containing a high quality biological molecule is added to a mixture comprising the decoy-coated beads, the bridger molecule, and the anti-target coated sensor (but no free decoy or no additional free bridger molecule), the output signal from that mixture can be plotted on the standard curve to determine, either relatively or precisely, how much high quality biological molecule is in the tested sample. In this embodiment, the high quality biological molecule is disrupting the competitive assay formation, and causing the beads to fall off the sensor.

Similarly, if a known quantity of the decoy or a known quantity of free anti-tag binding agent (i.e., not attached to a magnetic bead) is present in the mixture of FIG. 4, the amount of high quality biological molecule in the mixture (i.e., the mixture comprising the sample suspected of containing the high quality biological molecule, the decoy, the anti-tag coated beads, and the anti-anchor coated sensor) can be calculated by determining how much decoy or free anti-tag antibody was present in FIG. 4 and how much the output signal is reduced as compared to the output signal in the mixture without the sample (i.e., the mixture comprising the decoy, the beads, and the sensor, but without the sample suspected of containing the high quality biological molecule).

Additionally in the non-limiting configuration of FIG. 4, different amounts of the decoy or free anti-tag binding agent (i.e., not attached to a bead) may also be added to a mixture comprising the anti-tag binding agent-coated beads, the decoy, and the anti-anchor binding agent-coated sensor that does not contain any sample suspected of containing a high quality biological molecule, and the output signals can be recorded. These output signal measurements can be used to create a standard curve where the amount that the output signal decreases can be plotted against the amount of the added decoy or the added free anti-tag antibody.

This standard curve can then be used as a reference. In one non-limiting embodiment of the non-limiting configuration of FIG. 4, when a sample suspected of containing a high quality biological molecule is added to the mixture comprising the anti-tag binding agent-coated beads, the decoy, and the anti-anchor binding agent-coated sensor (but no additional decoy or no free anti-tag binding agent), the output signal from that mixture can be plotted on the standard curve to determine, either relatively or precisely, how much high quality biological molecule is in the tested sample. In this embodiment, the high quality biological molecule is disrupting the competitive assay formation, and causing the beads to fall off the sensor.

In various embodiments, if the background (e.g., non-specific binding of the bead to the sensor) is not consistent, but the shape of the standard curve is consistent, the quantity of the high quality biological molecule can be determined using the IC50 approach. For example, the IC50 from the curves are fit to each sample dilution series, and this will allow the samples to be compared to the standard curve without noise from background levels.

It should be noted that the change in the output signal when the mixture contains a high quality biological molecule will increase or decrease as compared to the control output signal depending on how the control competitive assay formation (i.e., no high quality biological molecule) is set up. Thus, depending on how the control (i.e., no sample) competitive assay formation is set up, the presence of a high quality biological molecule in a sample can cause the output signal to increase or decrease as compared to the output signal of the control competitive assay formation.

It should also be noted that the methods described herein can utilize two or more different tags, such that the same reagents can be utilized for any number of different biological molecules.

For example, FIG. 5 is a schematic diagram showing another non-limiting example of a competitive assay formation. The competitive formation shown in this FIG. 5 is similar to that shown in FIG. 4, where in FIG. 5, the anchor portion of the decoy is a second tag, namely a fluorescein moiety. Thus, in FIG. 5, the tag is polyhistidine (i.e., a His tag), the particle is a streptavidin-coated magnetic bead, the first binding agent is biotinylated anti-HIS antibody, the decoy is polyhistidine-tagged fluorescein, and the second binding agent (coated onto the sensor surface) is anti-fluorescein antibody. The sample contains polyhistidine-tagged recombinant protein from a transfection experiment that is being assessed for whether it is a high quality biological molecule (i.e., whether its His-tag is accessible), Accordingly, in FIG. 5, the competitive assay formation is formed by a mixture of ingredients comprising a first tag-specific antibody coated magnetic beads (where the first tag is the His tag), and a His tagged, fluorescein-tagged decoy that is presented to a second tag-specific antibody coated sensor surface (where the second tag is the fluorescein moiety). As shown in the upper right of FIG. 5, sample suspected of containing a high quality biological molecule is added to a mixture forming a competitive assay formation at any stage of the formation of the competitive assay formation. For example, the sample may be added first to a mixture containing the anti-His antibody coated beads under conditions where, if the tag is accessible, a high quality biological molecule:bead complex will form. This mixture may also contain the his-tagged fluorescein decoy, for example, in a known quantity. Bead:decoy complexes may then form, where the decoy forms a bridge linking the bead to the sensor to produce a competitive assay formation and result in a high output signal. However, if the high quality biological molecule is present in the sample, the formed high quality biological molecule:bead complex will not be specifically bound by the anti-fluorescein antibody coated sensor. The presence of a high quality biological molecule in the sample will thus result in a decreased output signal as compared to the output signal from the competitive assay formation (e.g., a formation comprising the decoy, the anti-His beads, and the anti-fluorescein sensor) formed in the absence of the sample. Where the amount of decoy present is the mixture forming a competitive assay formation comprising the sample is known, that amount can be used to calculate the amount of high quality biological molecule in the sample by calculating how much the output signal decreased as compared to the mixture forming a competitive assay formation in the absence of the sample.

Note that in the non-limiting configuration of FIG. 5, free anti-his tag antibody (i.e., not attached to a bead) or additional free decoy (i.e., free His-tagged Fluorescein decoy) can also be used to create a standard curve where the amount that the output signal decreases can be plotted against the amount of the added free anti-his antibody. To create this standard curve, a mixture of the anti-his coated beads, the anti-fluorescein coated sensor, and differing quantities of free anti-his antibody or additional free decoy are allowed to interact to form competitive assay formations, and the output signals from sensor are recorded and used to generate a standard curve plotting the amount of the free anti-his antibody or additional free decoy against the AMMP units. This standard curve can then be used as a reference to determine how much high quality biological molecule is in the tested sample (e.g., by adding the sample to a mixture of the anti-his coated beads, the anti-fluorescein coated sensor, and as known quantity of the decoy, and seeing where on the standard curve the resulting output signal falls to determine relatively or precisely how much high quantity biological molecule was in the tested sample.

Note that the output signal will decrease, leading to a positive result, only if the sample comprises a high quality biological molecule (i.e., if the biological molecule comprises an accessible His tag). However, if the His tag on the candidate target is inaccessible (i.e., if the candidate target is not a high quality biological molecule), a high number of competitive assay formations will form with the vast majority of the decoy molecules serving as bridges to form a competitive assay formation and specifically bind the beads to the sensor. Thus, the output signal will be very high, meaning a negative result (i.e., a result indicating there is no high quality biological molecule in the tested sample).

Figure 6B:
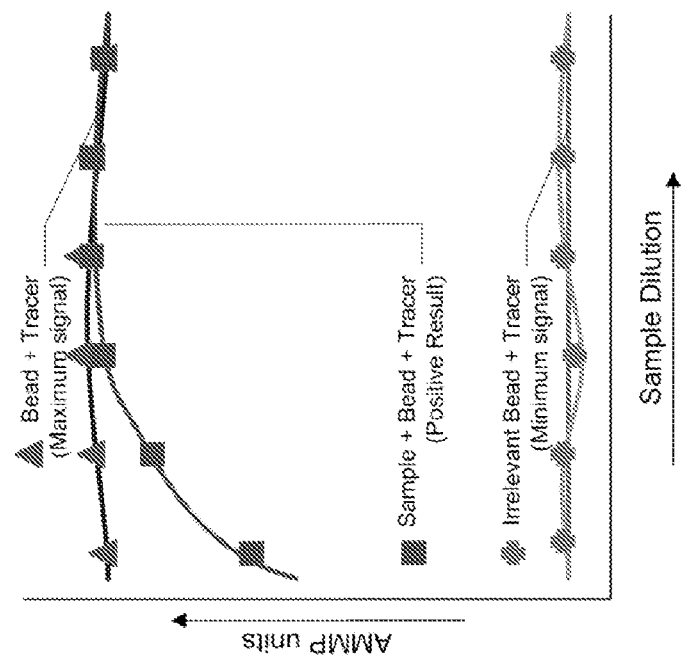
FIG. 6B is a line graph showing the results obtained in an AMMP assay when a high quality biological molecule is added to a competitive assay formation that disrupts the competitive assay formation. As shown by the blue triangles, the signal (in AMMP units using a ViBE instrument) with the competitive assay formation is high. When a high quantity of a sample comprising a high quality biological molecule is added, the competitive assay formation is disrupted (red squares). As the quantities of the high quality biological molecule are reduced (i.e., in FIG. 6B by diluting the sample comprising the high quality biological molecule), the disruption of the competitive assay formation is reduced, such that at low quantities of high quality biological molecule (i.e., at high dilution), the competitive assay formation is not disrupted at all. As a negative control, the green cross show the lack of formation of a competitive assay formation when an irrelevant bead (e.g., a microparticle coated with an antibody that does not specifically bind the target) is added.
Figure 6A:
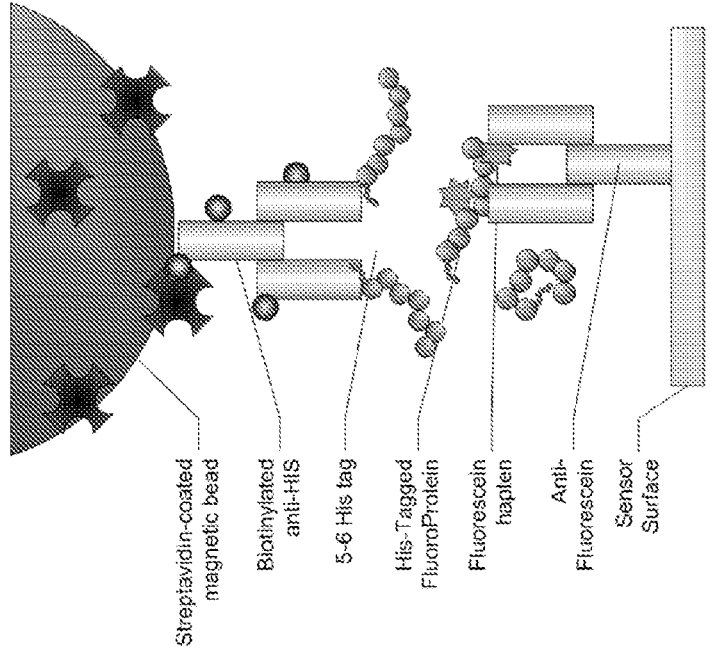
FIG. 6A is a schematic diagram showing the configuration of a non-limiting embodiment of a competitive assay formation that has been disrupted by a high quality biological molecule comprising an accessible tag and thus producing a positive result.

FIG. 6A is a schematic diagram showing the disruption of the competitive assay formation of FIG. 5 (comprising a His tag-specific antibody coated magnetic bead, a fluorescein tag-specific antibody coated sensor surface, and a His tagged, fluorescein-tagged decoy) with a high quality biological molecule from a sample. In FIG. 6B, the output signal of the AMMP assay is shown, where bead plus the decoy (referred to as a "Tracer" in FIG. 6B) results in a high output signal (blue triangles). When a sample is added (red squares; sample plus bead plus decoy Tracer), the output signal decreases because the high quality molecule in the sample competes with the decoy Tracer and disrupts the competitive assay formation of the decoy, the bead, and the sensor. However, the AMMP output signal eventually increases back to that maximum signal with increasing dilutions of the sample (i.e., signal output increases when the amount of sample is reduced). The green crosses show the non-binding (to the sensor) of an irrelevant bead and decoy Tracer.

Thus, as shown in FIGS. 6A and 6B, a positive result is indicated when less output signal is recorded and the HIS tagged proteins in the sample bind to the bead in preference to the HIS tagged Fluorescein decoy (Tracer) molecule. In other words, the His tagged proteins are high quality biological molecules and are able to compete with the decoy (in this case the His-Tagged FluoroProtein) in binding to the beads and reducing the number the competitive assay formations, thus reducing the number of beads specifically bound to the sensor and reducing the output signal.

In the absence of a high quality biological molecule comprising an accessible His tag, the decoy (i.e., the His-Tagged FluoroProtein—also called a Tracer molecule in FIGS. 6B and 7B) still bridges the beads to the sensor in a competitive assay formation giving a high output signal for binding. FIG. 7A is a schematic diagram showing the inability of an incorrectly folded recombinant protein (with an occluded HIS tag) to disrupt the competitive assay formation of FIG. 5 (comprising a His tag-specific antibody coated magnetic bead, a fluorescein tag-specific antibody coated sensor surface, and a His tagged, fluorescein-tagged decoy). In FIG. 7B, as in FIG. 6B, the output signal of the AMMP assay is shown, where bead plus the decoy (referred to as a "Tracer" in FIG. 7B) results in a high output signal (blue triangles). When a sample is added to the mixture (red squares; sample plus bead plus decoy Tracer), the output signal remains high, because the sample does not contain any high quality biological molecule that is capable of disrupting the competitive assay formation. The green crosses show the non-binding (to the sensor) of an irrelevant bead and decoy Tracer.

Note that in FIGS. 7A and 7B, the same negative result can occur when there is no His-tagged protein at all, as well as protein with inaccessible His tag.

In some embodiments, the decoy comprises at least a portion of the same target as the candidate target being screened. For example, if the recombinant protein whose expression as a high quality biological molecule whose expression is being detected and/or quantitated is a His-tagged interleukin-2 protein, the decoy may be, for example, a protein comprising a His tag coupled to at least a portion of the interleukin-2 protein.

It should be noted that in various aspects of the invention (e.g., the aspects as depicted schematically in the non-limiting configurations of FIGS. 1-7B and 15), the output signal is independent of the size of the high quality biological molecule. The high quality biological molecule need only be of similar size (e.g., within 100 kDa more or less, within 50 kDa more or less, or within 20 kDa more or less) to the bridger molecule (e.g., of FIG. 3), the tagged decoy (e.g., of FIG. 4), the His-tagged Fluorescein labeled decoy (e.g., of FIG. 5), or the His tagged anti-His antibody (e.g., of FIG. 15). The main characteristic of a high quality biological molecule as to whether the output signal will be changed (e.g., decreased) is the presence of an accessible tag in the high quality biological molecule.

In some embodiments, the decoy is unrelated to the recombinant protein whose expression is being detected and/or quantitated. The only relationship the decoy need have with the desired recombinant protein is that they both comprise the same tag (although both the decoy and the recombinant protein may comprise more than one tag). For example, as shown in the embodiment in FIG. 4, the decoy merely comprises an anchor and a tag. The "anchor" may be, for example, a fluorescein moiety while the "tag" may be, for example, a His tag. The sample to be screened may comprise recombinant His-tagged interleukin-2 molecules, some of which are high quality His-tagged interleukin-2 molecules. If the competitive assay formation is in the configuration shown in FIGS. 5, 6A, and 7A, the incorrectly folded His-tagged interleukin-2 molecules will not disrupt the competitive assay formation and the result shown in FIG. 7B will be obtained. If, on the other hand, the sample contains a high quality His-tagged interleukin-2 molecule, the His-tag on the interleukin-2 molecule will disrupt the competitive assay formation resulting in the results shown in FIG. 6B and leaving the fluorescein-tagged decoy attached to the anti-fluorescein antibody on the sensor surface (see FIG. 6A).

In some embodiments, the methods described herein, with appropriate controls, can be used to potentially detect aggregation of the expressed protein. For example, in some embodiments, a positive output signal may recorded where negative signal is expected (and is produced) with non aggregated expressed protein, but the non-aggregated expressed protein is not a high quality biological molecule. For example, a fluorescein hapten tagged anti-HIS antibody may be mixed in with the sample and beads post capture on the beads, without the decoy, to further identify aggregated expressed protein. In this case, bridges to the sensor would be from the HIS tag to the beads and from the alternately available HIS tag, on the captured protein molecule, to the sensor through the hapten tagged anti-HIS antibody (i.e., the bridger molecule). Positive signals result from aggregated protein where low signals result from non aggregated expressed protein. This embodiment is further described in the Examples below.

Data are shown below for *E. coli* and insect (SF9) cell expression systems with twelve proteins compared, with six unique proteins in each system. These data agree strongly with post purification ranking of the expressed proteins. Mammalian cell line expression can also be used with the disclosed methods.

In another non-limiting example, as described below, a unique decoy, Lipocalin1, has been selected for solubility and reliable background in lysate assays. In the approach described below, the decoy was coated (i.e., attached) to the bead and competed with the native lysate protein for anti-HIS antibody (that is tagged specific for the sensor surfaces). This configuration generates self-similar dilution curves from data that allow for ready numerical comparison (relative IC50 to the lipocalin1 standard dilutions) of expression level of a high quality biological molecule, namely an un-occluded HIS tagged fusion protein. In some embodiments, the invention provides methods for purifying and quantitating a properly folded (and thereby biologically functional) biological molecule. For example, as described below, a biological molecule such as a protein may be attached (e.g., covalently) to a tag. Although the His tag is described below, any such tag may be utilized.

Figure 15:
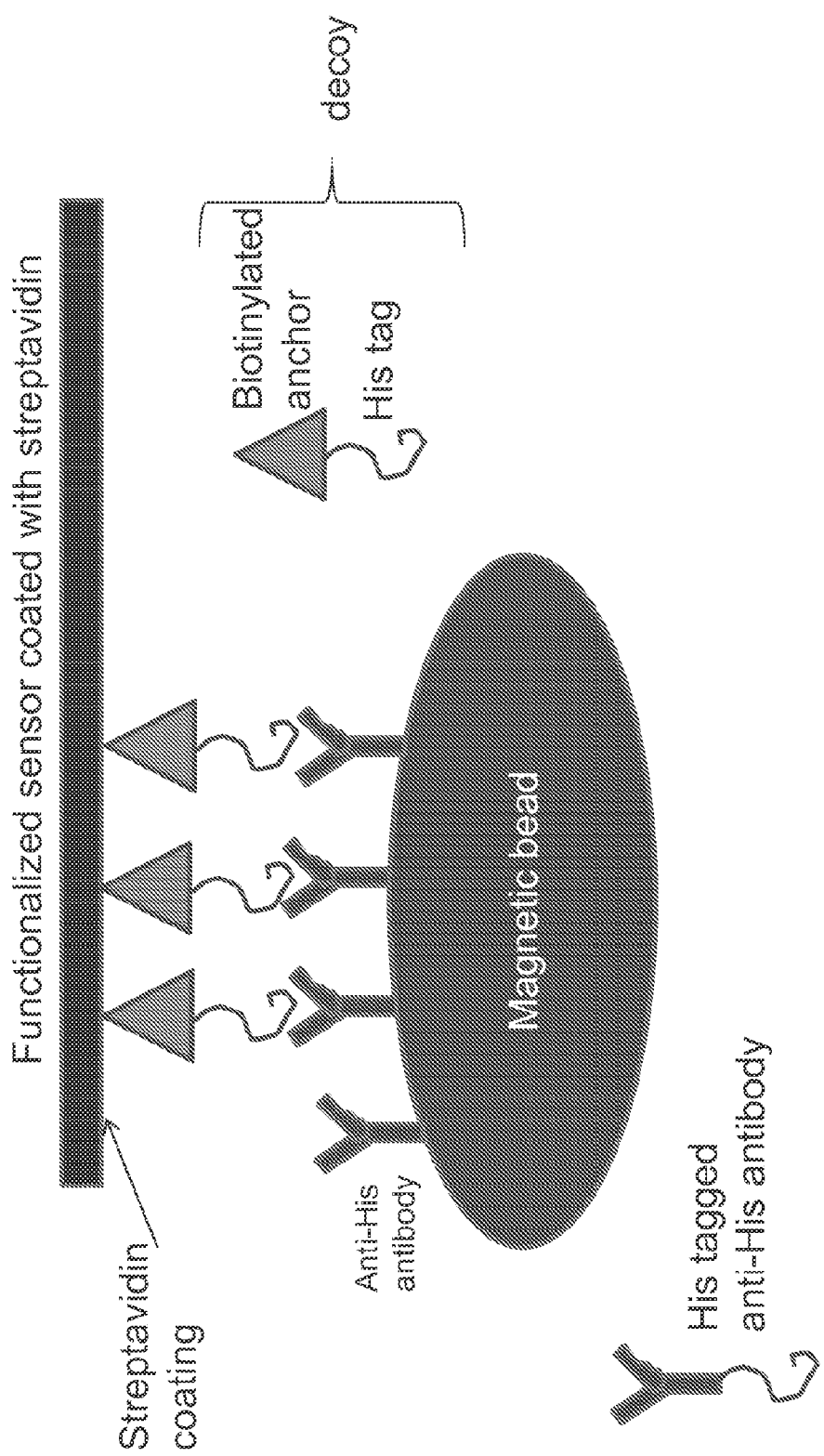
FIG. 15 is a schematic diagram showing a non-limiting embodiment of a competitive assay formation. In this configuration, the competitive assay formation consists of sensor coated with the decoy, where the His-tag of the decoy is accessible, and magnetic beads coated with anti-His antibody. A competitive assay can also be formed in this configuration via a His-tagged anti-His antibody.
Figure 17:
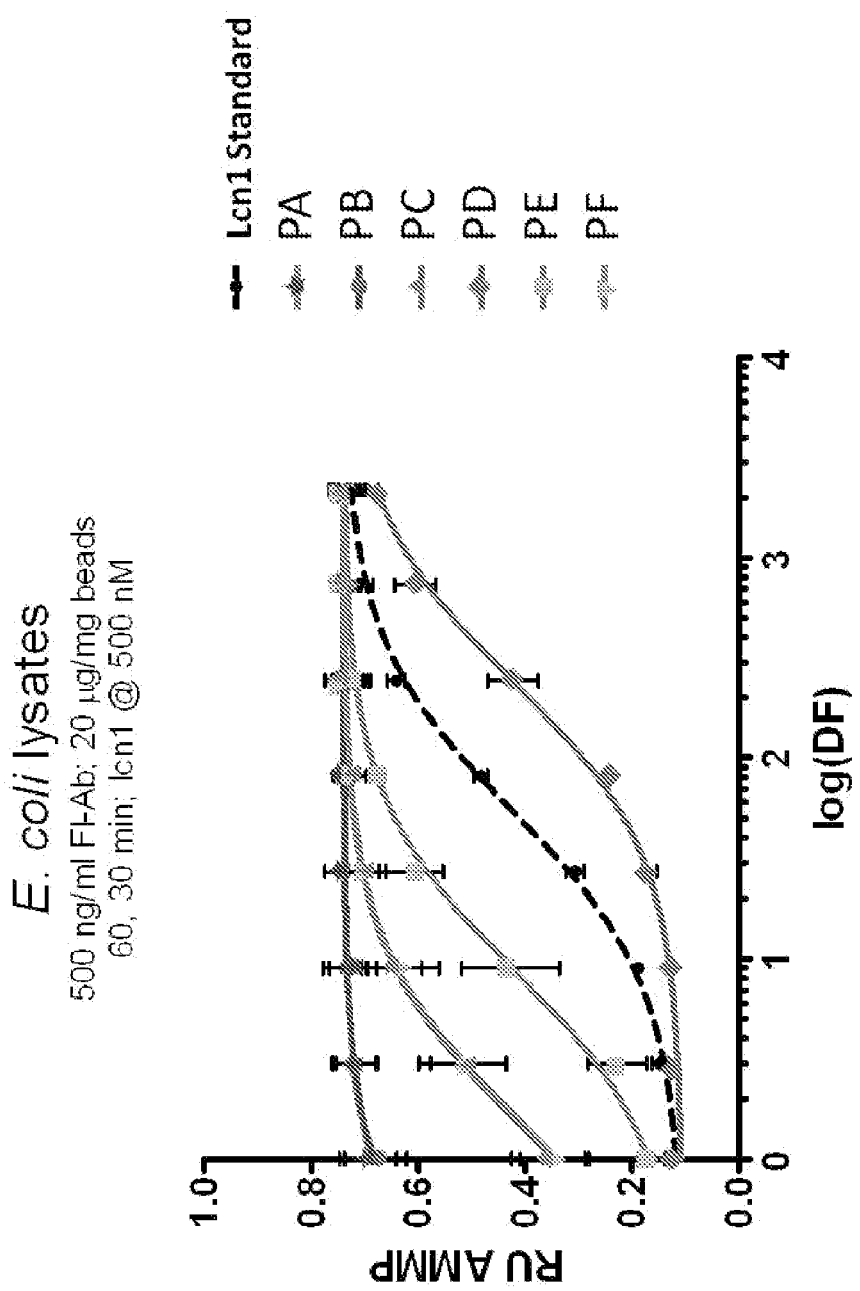
FIG. 17 is a line graph showing the AMMP results obtained from six different recombinant cytosolic proteins expressed by *E. coli* as compared to the Lipocalin 1 decoy.
Figure 18:
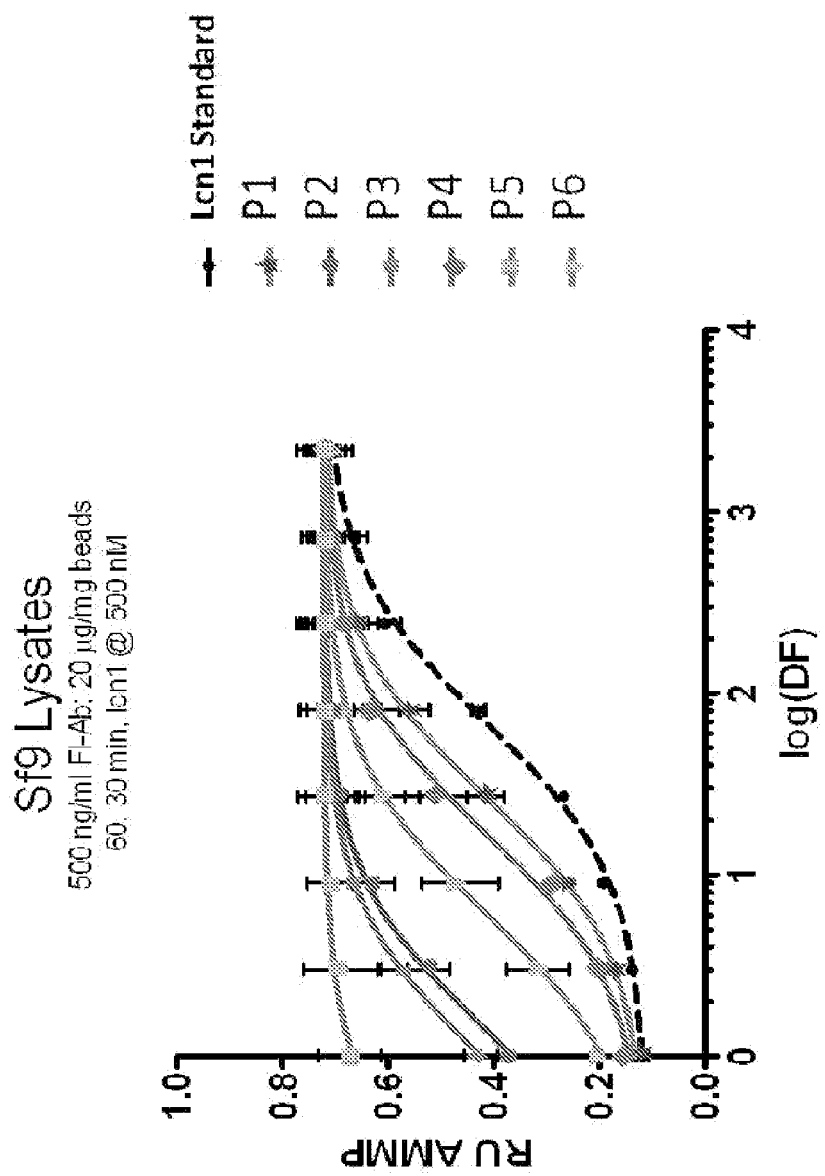
FIG. 18 is a line graph showing the AMMP results obtained from six different recombinant cytosolic proteins expressed by insect cells as compared to the lipocalin1 decoy standard.
Figure 19:
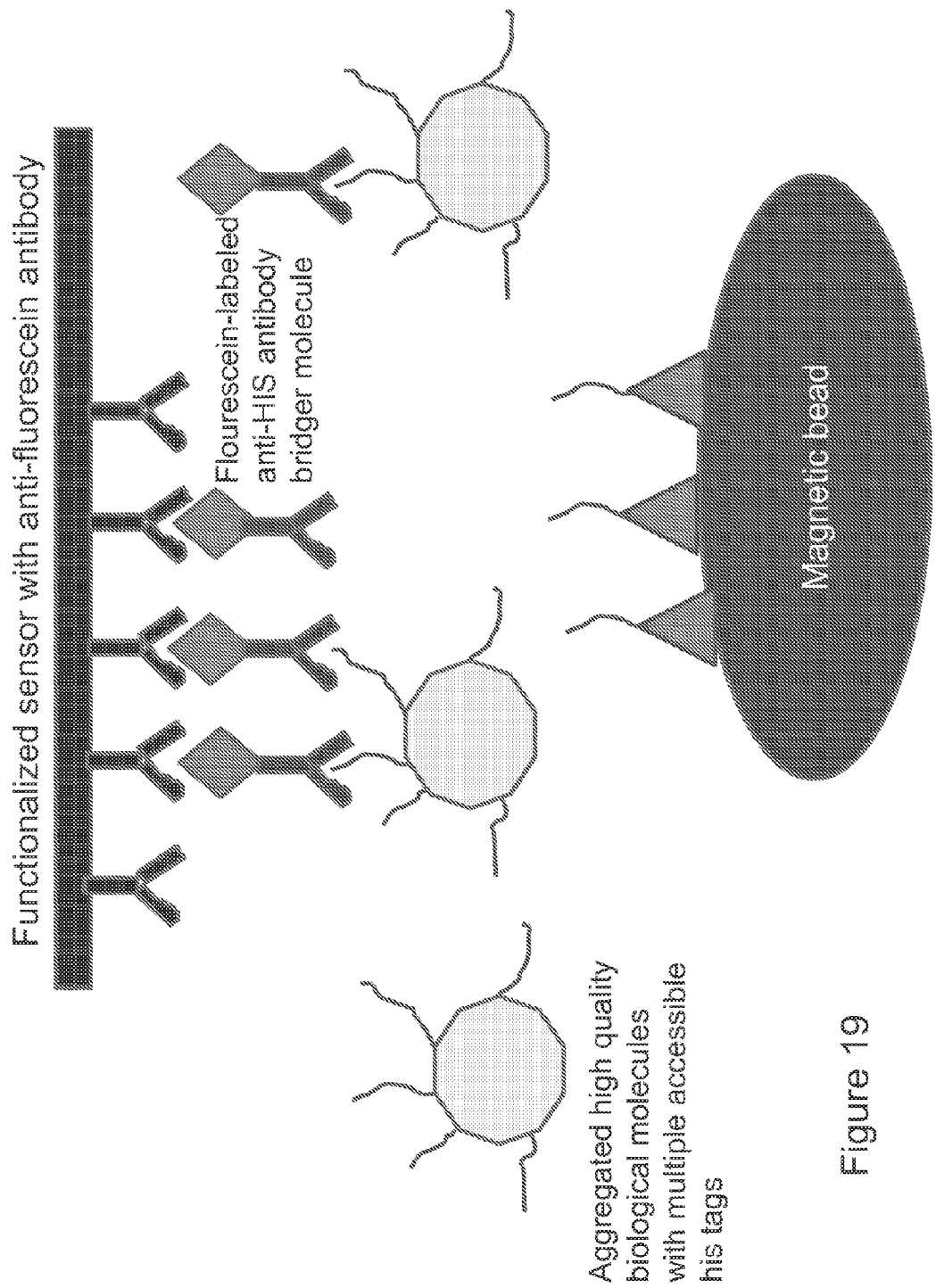
FIG. 19 is a schematic diagram showing the disruption of the competitive assay formation of FIG. 3 with an aggregated biological molecule having multiple accessible His tags. As noted in the FIG. 19, the disruption can be from the complex of the aggregated high quality biological molecule:bridger molecule binding to the sensor, or the aggregated high quality biological molecule:bridger molecule complex not binding to the sensor. In either scenario, the bead no longer specifically binds to the sensor, thereby changing the output signal of the sensor.

It should be noted that in various embodiments of the invention, the quantity of a high quality biological molecule in a sample can be determined by reference to a standard curve made from anti-tag antibody attached to a target molecule (e.g., in the configuration of FIG. 3), the tagged decoy (e.g., in the configuration of FIG. 4), the His-tagged Fluorescein labeled decoy (e.g., in the configuration of FIG. 5), or the His tagged anti-His antibody (e.g., in the configuration of FIG. 15). For example, in the non-limiting embodiment of FIG. 3, where the decoy is a His-tagged Lipocalin1, FIGS. 17 and 18 show the standard curve of the free decoy, added to the mixture of tagged decoy coated magnetic bead, anti-tag antibody attached to a target molecule that is presented to the anti-target antibody coated sensor, at the indicated dilution factors (the black circles with the curve shown in a dashed black line). As can be seen from the indicated dilutions, the output signal is decreased (meaning the beads are competed off the sensor by the free decoy) at high concentrations of free decoy. However, as the free decoy is diluted, the less free decoy is available to compete with the beads, and so at the highest dilutions (e.g., log (DF) of approximately 3.2), the output signal is very high, meaning there is very little free decoy in the mixture. As described above, this standard curve can be used to determine how much high quality biological molecule is in a tested sample by simply plotting the output signal emitted from a sensor from a mixture containing the tested sample to the standard curve. This is further discussed in the examples below, particularly Example 3.

It should be noted that in various embodiments of the invention, the assay may be tailored such that an increase in the output signal is emitted by a sensor from a mixture containing a high quality biological molecule as compared to a control output signal from a control sensor (e.g., from a mixture that does not contain a high quality biological molecule). The change (increase or decrease) in the output signal in the presence of a high quality biological molecule will depend upon what is used to generate the control output signal. In the embodiments of the invention depicted in the accompanying figures, a competitive assay formation is what is used to generate the control output signal. However, the skilled artisan would understand that a control output signal can just as easily be derived from the lack of a competitive assay formation. This would result in a very low control output signal. The presence of a high quality biological molecule may result in the formation of a competitive assay formation, leading to a high output signal. For example, in the configuration shown in FIG. 2, a control output may be derived from the mixture of an anti-tag coated sensor and the anti-target coated beads. From this mixture, no competitive assay formation will be formed, and the output signal will be low. However, the addition of a high quality biological molecule will form a competitive assay formation by causing the beads to bind to the sensor via the high quality biological molecule. Thus, the output signal in the presence of the high quality biological molecule will be higher than the control output signal.

In some embodiments, the methods of the invention are useful in detecting the presence of an active mature protein in a sample. Note that in addition to a sample from a cultured recombinant cell, any sample suspected of containing a high quality biological molecule or am active mature protein can be used. For example, biological samples including, without limitation, tissue biopsy samples (e.g., from a cancer), blood, pleural effusion samples, saliva, tears, urine, serum, plasma, semen, breast milk, and synovial fluid may be screened using the methods described herein.

Many biological molecules are present as inactive precursors. An inactive precursor of an active mature protein is called a zymogen. A zymogen may also be the inactive precursor of an active mature protein that has enzymatic activity. In some embodiments, a zymogen comprises at least two portions, one of which includes the active mature protein, and must be cleaved to release the active mature protein. In some embodiments, a zymogen is inactive because it has a different conformation than the active mature protein and must be subjected to a biochemical change (e.g., a change in the pH environment of the zymogen) to change it into its active mature protein. Regardless of whether the active mature protein is released by cleavage of the zymogen or by a conformational change of the zymogen, the zymogen is still said to comprise a mature protein portion.

Some non-limiting zymogens and their mature proteins include hormones (e.g., insulin, oxytocin, vasopressin, angiotensin (i.e., angiotensin II produced by cleaving the two C-terminal residues from angiotensin I), members of the caspase protease family (e.g., caspase 2, caspase 9, and caspase 7), members of the coagulation system, members of the complement system, and digestive enzymes: inactive chymotrypsinogen (which is cleaved by trypsin and other enzymes to produce active chymotrypsin), inactive pepsinogen (which is cleaved to produce active pepsin), and inactive trypsinogen (which is cleaved to produce active trypsin).

The following examples are provided to illustrate, but not to limit, the invention.

Example 1

Detection and Quantitation of High Quality Biological Molecules, Namely, High Quality his-Tagged Proteins, Expressed by Recombinant E. coli and Recombinant Insect Cells Using an HIS Antibody-on-Beads AMMP Assay Configuration for a Competition Assay To determine whether the methods described herein can be used for detection and quantitation of recombinant proteins produced in cell expression systems from various species, His-tagged proteins were expressed in E. coli cells and SF9 insect cells. To do this, the following methods were used.

Materials and Methods

Bead preparation: One hundred microliter aliquots of magnetic microbeads ($6-8 \times 10^8$ beads/ml, Dynabeads® M280 Streptavidin, Invitrogen Dynal) were washed three times with 500 uL volumes of 0.2M phosphate buffer containing 150 mM NaCl and 0.05% Tween-20 (PBST). The washed beads were brought to a volume 500 uL PBST in 1.5 mL conical microcentrifuge tubes, then conjugated to biotinylated anti-pentahistidine antibody (catalog #34440, Qiagen, Inc.) at concentrations of 5-, 2-, 1- or 0.5 µg antibody per mg bead slurry (approximately $6 \times 10^8$ beads/mg). The antibody-bead mixtures were incubated with gentle end-over-end rotation at 22° C. for thirty min, then washed as above (3×500 µL PBST) by first washing bead slurry with five volumes phosphate buffered saline containing 0.05% Tween-20 (PBST). Unoccupied streptavidin sites are filled, by incubation of the washed antibody-loaded beads with 10 µg biotinylated bovine serum albumin (BSA). The antibody-loaded, blocked beads are again washed (3×500 uL PBST), then stored at 4° C. for later use.

Tracer (i.e., Decoy) preparation: Protein X is an NTA-nickel purified human N'-terminal hexahistidine fusion protein (MW 20,600 daltons). One hundred micrograms Protein X was buffer exchanged to 50 mM borate buffer, pH 7.2 by desalting over PD-10 'spin' column (catalog #17-0851-01, GE Healthcare), then reacted 1 hr with a 10-fold molar excess of N-hydroxysuccinimidyl-fluorescein (NHS-Fluorescein) at 22° C. The reaction was halted, and non-reacted NHS-fluorescein removed from the resulting tracer (i.e., decoy) by centrifugation through a PD-10 spin column (as above). The resulting 'flow-through' fractions were collected and quantified for total protein and fluorescein:protein ratio by spectrophotometric analysis, then stored in 0.2M phosphate buffered saline containing 0.05% bovine serum albumin at 4° C. for later use.

Sample characterization: A series of six Escherichia coli- and six baculovirus-driven insect cell lysates, each encoding for a different human protein-hexahistidine affinity tag fusion protein are given in this example (Tables 1 and 2). Total protein concentration for each lysate was determined by microBCA analysis, and several aliquots of each lysate were prepared at 10 ug/ml total protein. SDS-PAGE gels (10 ug/lane) permitted visualization of the proteins present in each lysate. Western immunoblots were also obtained for each lysate, using the anti-pentahistidine antibody described above, and visualized with alkaline-phosphatase conjugated anti-mouse IgG (heavy and light chains) and BCIP-NTB.

Principles of the AMMP assay: This technique measures the ability of an unknown fusion protein, putatively containing an N'- or C'-terminal sequence of 4-10 histidine residues, to competitively inhibit the binding of a similarly expressed, fluorescein-labeled fusion protein (i.e., the Protein X decoy or tracer) that is known to possess an accessible N'-terminal hexahistidine sequence to anti-hexahistine antibodies immobilized on the surface of paramagnetic beads. Signal is generated in the system when the fluorescein-labeled tracer molecule 'bridges' the anti-hexahistidine-coupled beads to the anti-fluorescein-coupled sensor surface to form a competitive assay formation—the frequency at which the sensor membrane vibrates decreases in direct proportion to the increased mass (provided by the bead) bound to the sensor surface (see, e.g., FIGS. 5-7B). Non-specifically bound materials were washed from the sensor surface using a slow (70 microLiter/sec) flow of running buffer (0.2M phosphate buffer, containing 0.45M NaCl and 1% (v/v) Tween-20). Between determinations, the sensor surface was regenerated using a similar flow of 0.02M phosphoric acid, followed by neutralization (six volumes of running buffer), to prepare for the next samples.

For analysis, 10 ug/mL aliquots of each lysate plus a 10 µg/mL aliquot of the ProteinY standard are serially diluted into PBST (3-fold, through 8 places). Eighty microliter samples from each dilution series are dispensed into each of three columns (1, 2, and 3) in a standard 96-well microplate; column 4 contains 80 ul PBST-only. Twenty µL bead suspension (1.5e5 beads/well) is dispensed to columns 1-4, and 20 uL tracer (20 ng/mL) is dispensed to each well in columns 2-4, thus making Column 1=NSB control, Columns 2-3='TEST', and Column 4='MAX Signal'. This matrix is repeated for each of the 12 samples. The resulting plates are incubated, shaking, on the ViBE Protein Analysis Platform, and the instrument is started.

Results

Bead selection and tracer (i.e., decoy) titration studies: Each of the antibody-conjugated bead lots were assessed for tracer (i.e., decoy) binding capacity by incubating in the presence of serially diluted tracer (fluorescein-labeled, his-tagged protein). When using beads loaded with 0.5 ug anti-pentaHIS antibody, a tracer (i.e., decoy) $ED_{50}$ value approaching $3 \times 10^{13}$M was observed with saturation occurring at concentrations in excess of $5 \times 10^{11}$M. From this data a concentration of 0.5 anti-pentaHIS antibody per mg beads was selected, and a concentration of 1 nM tracer (roughly $ED_{80}$), thus targeting sensitivity in the nanomolar range for incoming samples.

AMMP assays: Prior to testing all samples were centrifuged for 10 min at 17,000 RCF to eliminate particulates and/or insoluble protein. The samples were normalized to a nominal total protein concentration of 10 ug/ml, then serially diluted as stated above. An assay was considered valid if the MAX sample (bead+decoy) signal attained was greater than or equal to 0.7 relative AMMP units, the NEG sample (bead only) signal was less than or equal to 0.3 relative units, and any observable NSB sample signal was less than 0.5 relative units. Data was plotted (relative AMMP units vs. log(dilution)) for each sample and for the assay standard (Protein Y). Unknown sample concentrations were back-calculated from the performance of the standard data, reduced by non-linear regression using standard four-parameter curve fitting program.

Each sample was tested a total of nine times (3 days×3 analysts), with typical results as shown in FIGS. 8-11.

Figure 8:
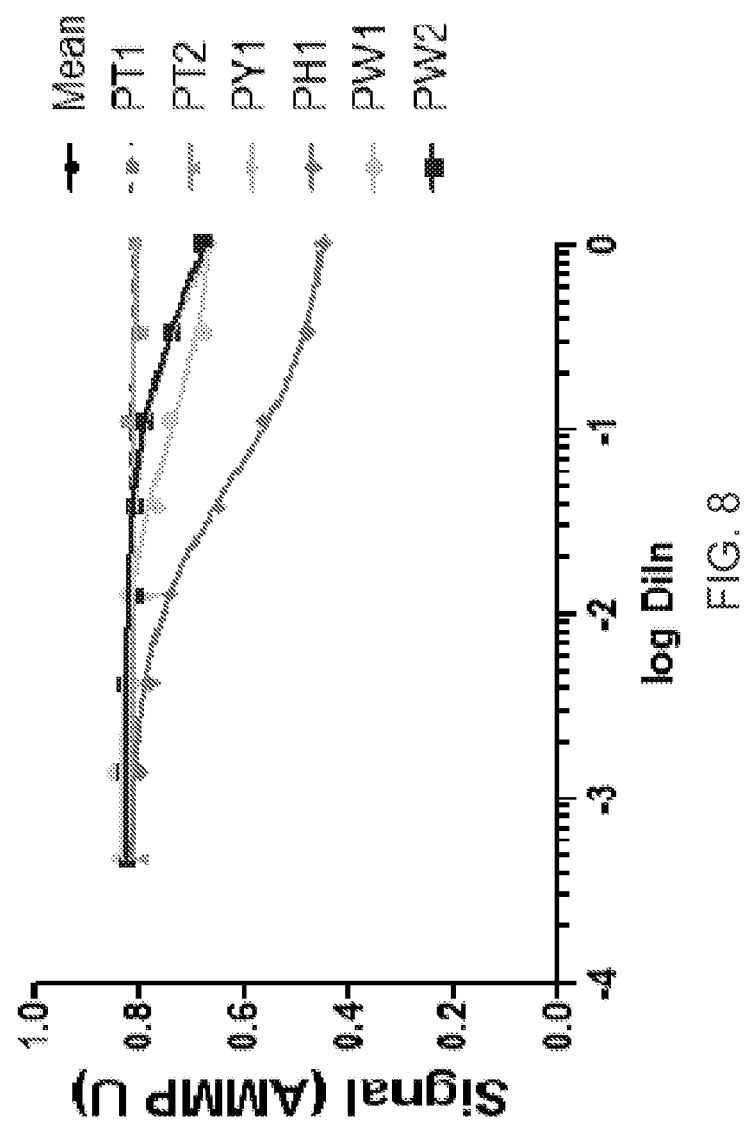
FIG. 8 is a line graph showing the AMMP results of recombinant proteins PT1, PT2, PY1, PH1, PW1, and PW2 expressed by *E. coli* as compared to the AMMP results obtained by the decoy ("Mean").
Figure 9:
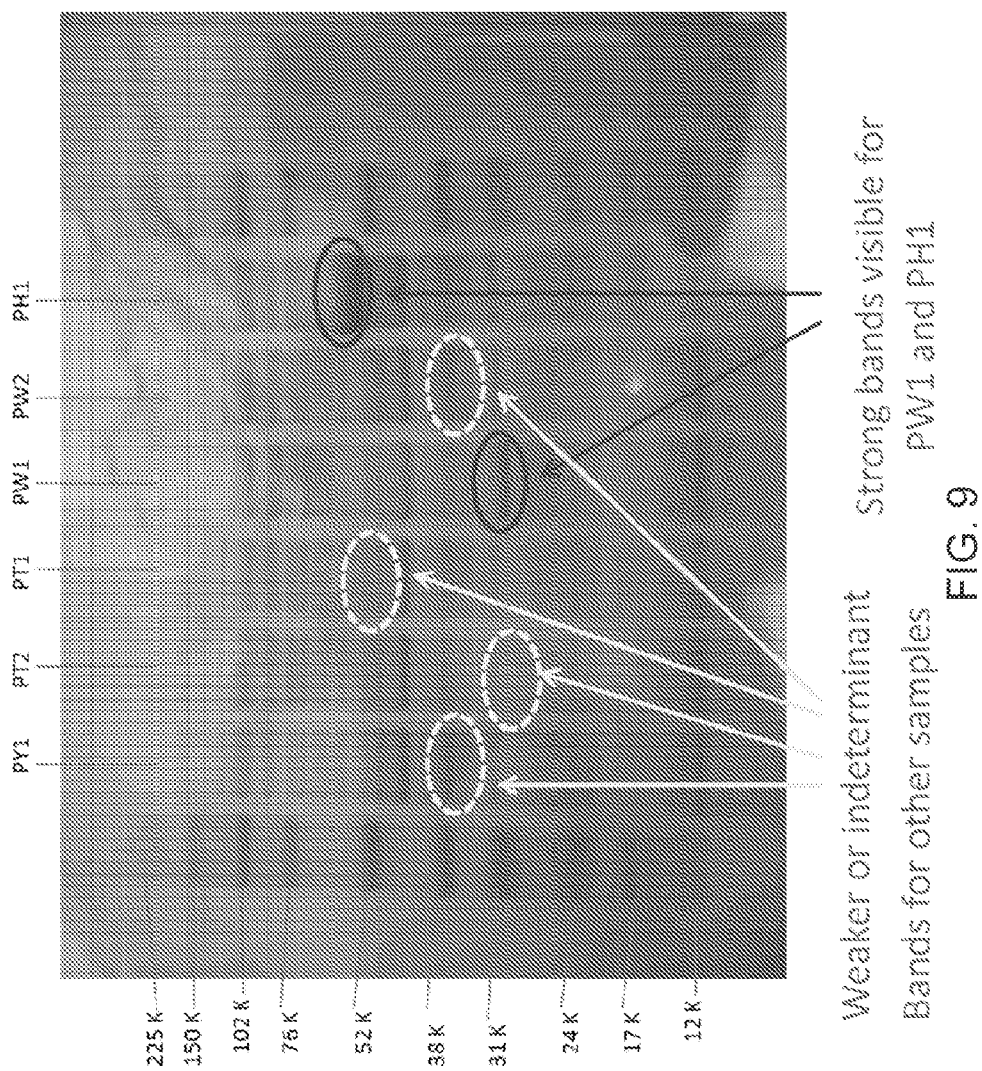
FIG. 9 is a silver stain gel showing the amount of recombinant proteins PT1, PT2, PY1, PH1, PW1, and PW2 expressed by *E. coli*.

FIGS. 8 and 9, as well as Table 1, present the data for *E. coli* lysates. FIG. 8 presents typical results for sample dilution to 15 ug/ml, then serial diluted 3-fold through 8-fold. Controls were run (data not shown) for Bead only (NEG), Bead+Sample (NSB), IrrevBead+Sample, Bead+Tracer (MAX). Visual inspection of the resulting plot permits the assignment of rough 'rank order' to the *E. coli* lysate samples—PH1>PW1>PY1≈PW2>PT1≈PT2. The use of purified, his-tagged Protein Y as a standard in the assay permitted further quantification of the samples. In FIG. 8, the data for the tracer decoy is subjected to non-linear regression analysis and fitted to the four-parameter logistic equation: $y=(A-D)/(1+(x/C)^B)+D$, where A=signal maximum, B='Hill slope', C=log(ED50), D=signal minimum, and x=log(dilution factor) to calculate the ED50 concentration of Protein Y (shown in FIG. 8 as "Mean"). Since Protein Y and the unknown lysates are also plotted as signal vs. dilution, fitting these data to the four-parameter logistic plot permits the potency of each sample relative to Protein Y. FIG. 9 presents a typical gel, which confirms the results shown in FIG. 8.

These data are tabulated in Table 1. As discussed above, the AMMP rank is based on IC50 determined from dilution curves and is consistent with visual inspection. The rankings listed are based on measurements made with samples normalized for total protein level. Most samples had similar total protein levels, so accounting for dilution factor would not change the ranking. Rather, it would give PH1 a stronger #1 ranking.

Figure 10:
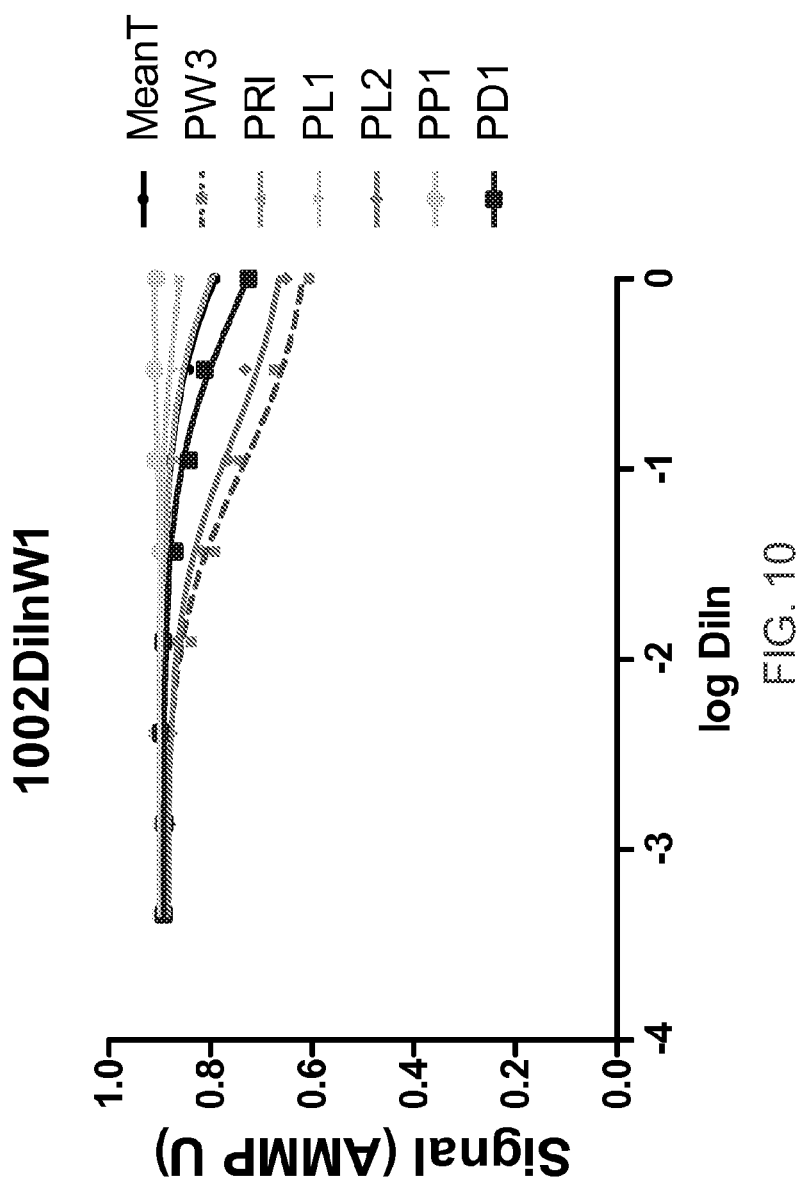
FIG. 10 is a line graph showing the AMMP results of recombinant proteins PW3, PR1, PL1, PL2, PP1, and PD1 expressed by insect cells as compared to the AMMP results obtained by the decoy ("MeanT").
Figure 11:
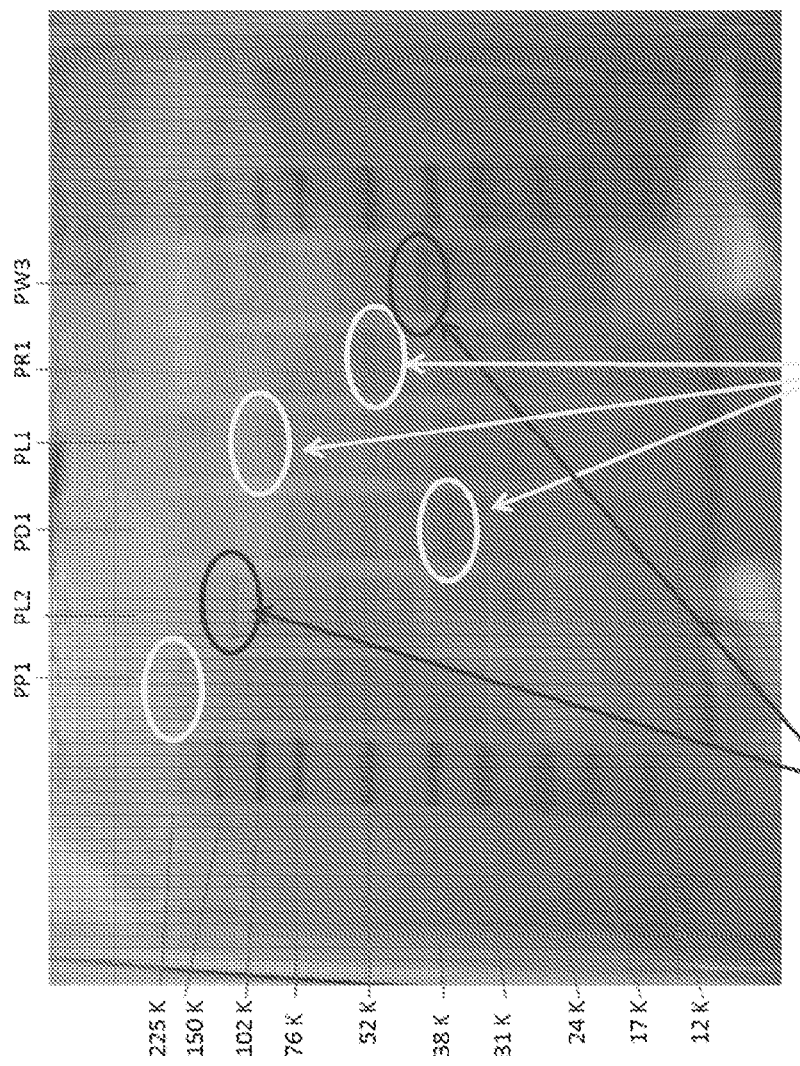
FIG. 11 is a is a silver stain gel showing the amount of recombinant proteins PW3, PR1, PL1, PL2, PP1, and PD1 expressed by insect cells.

FIGS. 10 and 11, as well as Table 2, present the data for insect lysates. FIG. 10 presents typical results for sample dilution to 15 ug/ml, then serial diluted 3-fold through 8-fold. Controls were run (data not shown) for Bead only (NEG), Bead+Sample (NSB), IrrevBead+Sample, Bead+Tracer (MAX). Visual inspection of the resulting plot permits the assignment of rough 'rank order' to the insect lysate samples—PW3>PL2>PD1>PR1>PL1≈PP1. The use of purified, his-tagged Protein Z (shown in FIG. 10 as "MeanT") as a standard in the assay permitted further quantification of the samples. In FIG. 10, the data for the tracer decoy is subjected to non-linear regression analysis and fitted to the four-parameter logistic equation: $y=(A-D)/(1+(x/C)^B)+D$, where A=signal maximum, B='Hill slope', C=log(ED50), D=signal minimum, and x=log(dilution factor) to calculate the ED50 concentration of Protein Z. Since Protein Z and the unknown lysates are also plotted as signal vs. dilution, fitting these data to the four-parameter logistic plot permits the potency of each sample relative to Protein Z (i.e., relative to MeanT). FIG. 11 presents a typical gel, which confirms the results shown in FIG. 10.

These data are tabulated in Table 2. As discussed above, the AMMP® rank is based on IC50 determined from dilution curves and is consistent with visual inspection. The rankings listed are based on measurements made with samples normalized for total protein level. Most samples had similar total protein levels, so accounting for dilution factor would not change the ranking, except for PR1.

TABLE 2

| | Insect Lysates | | | | | |
|---|---|---|---|---|---|---|
| ID | PW3 | PR1 | PL1 | PL2 | PP1 | PD1 |
| MW (daltons) | 37100 | 48600 | 96800 | 121100 | 235000 | 35600 |
| His orientation | N' | C' | C' | C' | N' | N' |
| Cells (×1e6) | 191 | 124 | 97 | 122 | 99 | 105 |
| Protein (mg/ml) | 12.30 | 14.60 | 11.20 | 10.50 | 10.60 | 18.30 |
| Gel band strength | 1 | +/− | +/− | 2 | +/− | 3 |
| AMMP ® Rank | 1 | 4 | — | 2 | — | 3 |

Data: Mouse, *E. coli*, and Human Samples

Figure 12:
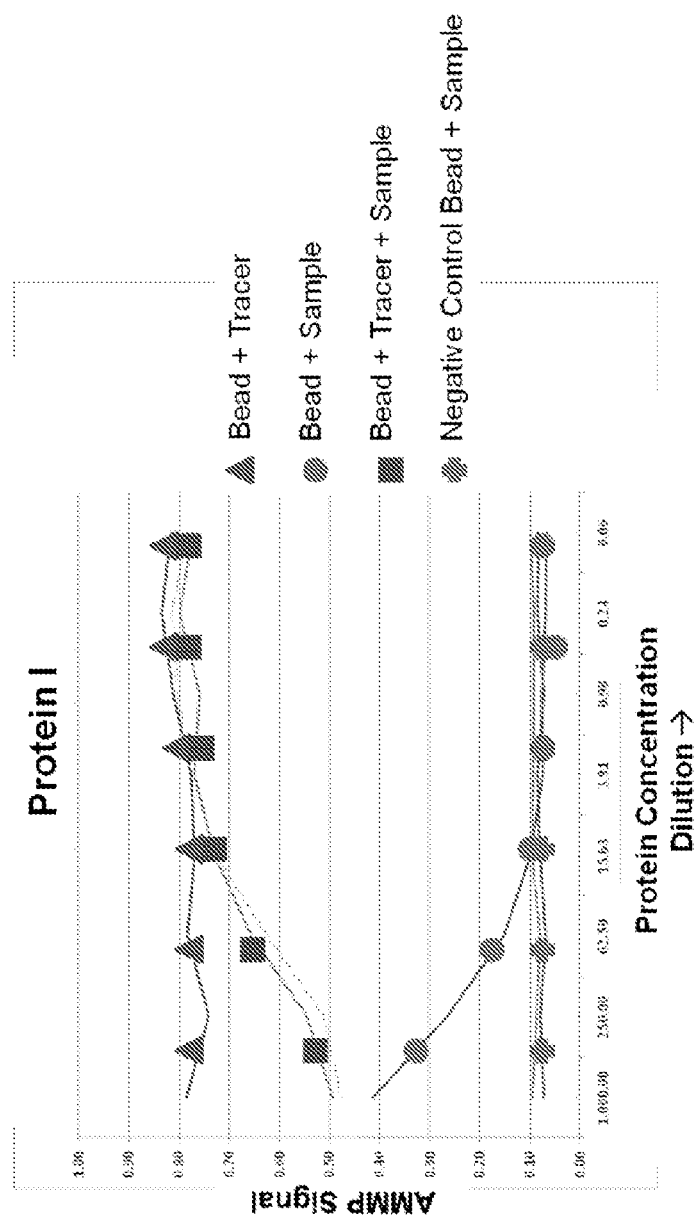
FIG. 12 is a line graph showing the AMMP results from a non-limiting protein, namely protein 1.
Figure 13:
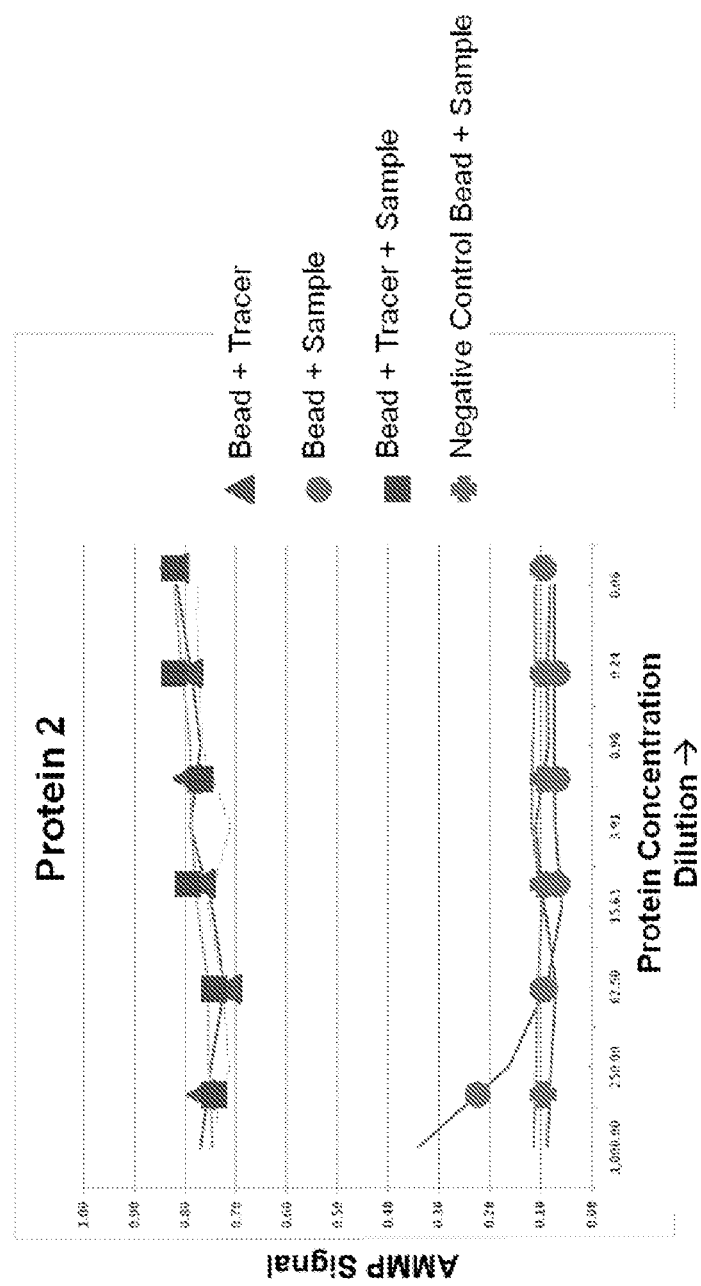
FIG. 13 is a line graph showing the AMMP results from a non-limiting protein, namely protein 2.
Figure 14:
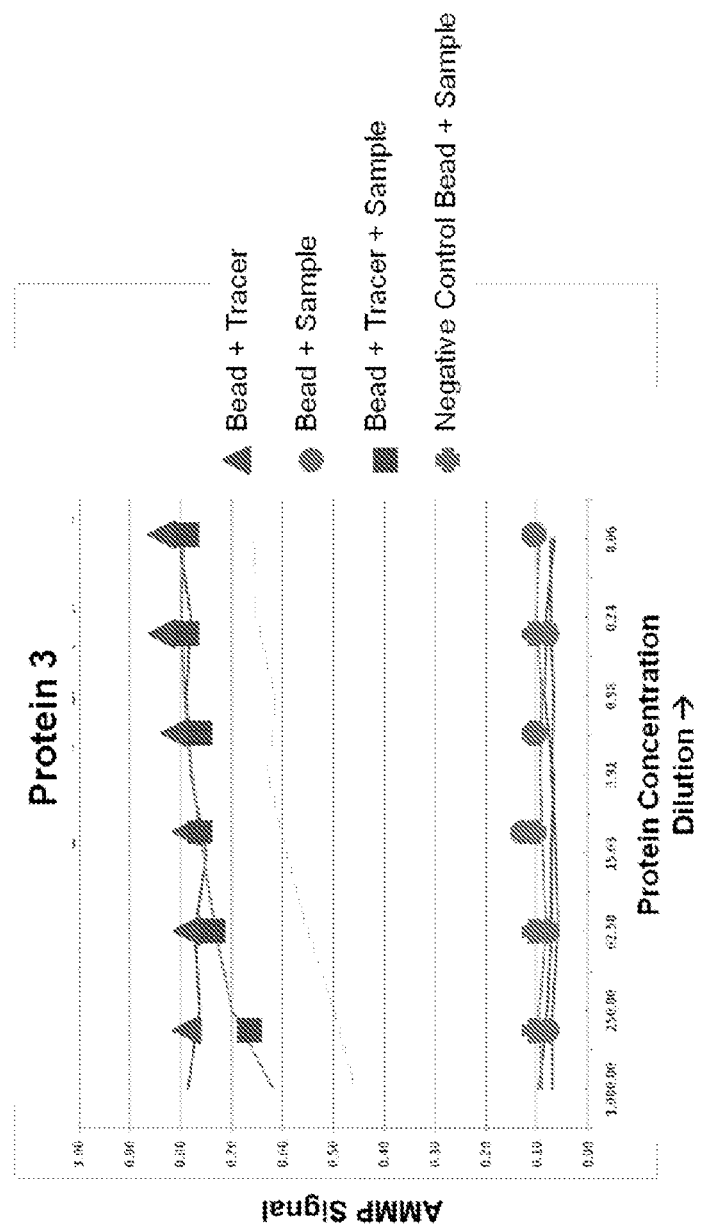
FIG. 14 is a line graph showing the AMMP results from a non-limiting protein, namely protein 3.

FIGS. 12-14 show three samples from mouse (FIG. 12, "Protein 1"), *E. coli* (FIG. 13, "Protein 2"), and human (FIG. 14, "Protein 3") sources. The sample preparation and analysis was essentially the same as the *E. coli* and Insect Lysates example described above.

Proteins 1 and 3 (FIGS. 12 and 14, respectively) show positive results for bead+tracer+sample compared to the controls, with protein 1 showing signal bead plus sample alone without tracer decoy. This behavior is replicated in protein 2 (FIG. 13), but there is no signal for the bead+tracer+sample below the bead+tracer combination. Denatured gels (data not shown) report all three proteins have the expected size. Native gels (data not shown) run on all three proteins indicate that protein 3 gives its protein size as expected while proteins 1 and 2 give bands that indicate possible aggregation. In the AMMP data for protein 2 the sample is undetectable as a positive signal (where signal for beads+tracer+sample would be below the beads+tracer control). These results suggest that protein 2 may be difficult to

TABLE 1

| | *E. coli* Lysates | | | | | |
|---|---|---|---|---|---|---|
| ID | PT1 | PT2 | PY1 | PH1 | PW1 | PW2 |
| Mol. Weight (daltons) | 50100 | 27400 | 36000 | 59300 | 31700 | 35600 |
| His orientation | N' | N' | C' | N' | C' | N' |
| Wet weight (g) | 0.8 | 0.9 | 0.9 | 0.9 | 0.4 | 1.0 |
| Protein (mg/ml) | 11.96 | 8.14 | 11.45 | 25.76 | 9.42 | 10.06 |
| Gel band strength | — | — | +/− | 1 | 2 | +/− |
| AMMP ® Rank | — | — | 4 | 1 | 2 | 3 | purify, even though HIS tag maybe available as indicated by the beads+sample negative control having elevated signal over the expected background for non-aggregated protein.

Overall results indicate that HIS tagged protein is detectable in the ng's-ug's per milliliter range. Results also indicate that beads+sample signals that are positive above the negative control beads+sample signals at low dilutions are correlated to aggregated protein in sample. This is advantageous to know as this can adversely affect purification effectiveness.

Example 2

Detection and Quantitation of his-Tagged Proteins Expressed by Recombinant Mammalian Cells COS cells (monkey kidney fibroblast-like cells), CHO cells (Chinese hamster ovary cells) and HeLa (human cervical cancer cells) are purchased (e.g., from the American Type Culture Collection (ATCC), Manassas, Va.) and cultured in standard conditions (e.g., 10% fetal bovine serum in RPMI 1640 media).

Expression vectors encoding His-tagged proteins are generated. Any expression vector can be used. Three different human proteins are used, one cytosolic (namely the syk kinase), one transmembrane (namely the CD2 receptor), and one secreted (namely interleukin-2).

Nucleic acid sequences encoding these proteins are known. For example, the human syk kinase-encoding cDNA sequence can be found at NCBI Reference Sequence: NM_003177.5 (see also Ghosh et al., J. Biol. Chem. 287 (15), 11833-11841 (2012)). Similarly, the human CD2-encoding cDNA sequence can be found at GenBank Accession No. M16445.1 (from the NCBI; see also Seed and Aruffo, Proc. Natl. Acad. Sci. USA 84(10): 3365-3369, 1987). The human interleukin-2 encoding cDNA sequence can be found, for example, at NCBI Reference Sequence: NM_000586.3 (see also Bazan, J. F., Science 257 (5068), 410-413, 1992 and Purvis et al., Cell. Immunol. 144 (1), 32-42, 1992.

The pcDNA6/V5-HisA, pcDNA6/V5-HisB and pcDNA6/V5-HisC vectors will be purchased from Life Technologies (Carlsbad, Calif.) and nucleic acid sequences of interleukin-2, CD2, and syk kinase are inserted to produce expression vectors encoding these proteins tagged at their C-terminus with the His tag.

The pCMV6-AN-His vector will be purchased from Origene (Rockville, Md.; catalog no. PS100011) and nucleic acid sequences of interleukin-2, CD2, and syk kinase are inserted to produce expression vectors encoding these proteins tagged at their N-terminus with the His tag.

Each of these vectors will be transfected (using, for example, CaPO4 precipitation, electroporation, lipofectin reagent, or DEAE-dextran) into each of the COS cells, CHO cells, and HeLa cells so that in total 18 transfections will be performed.

The resulting transfections are serially diluted into 96 well tissue culture plates such that a single cell is plated into each well, and the resulting cells ("colonies") are clones of the starting cell. For the colonies transfected with the IL-2 constructs (i.e., His-tagged at the N'terminus or at the C'terminus), culture media in which the cells are growing are collected and screened as samples, because the recombinant protein is expected to be secreted into the culture media. For the colonies transfected with the transmembrane CD2 fusions and the cytosolic syk kinase fusions, an aliquot is taken from each colony, lysed, and the lysates are screened as samples.

His tagged protein standards (the 'decoy' or 'tracer') are similarly made. There are six decoys, tagged on either the N'terminus or C'terminus and expressed in COS, CHO, or HeLa cells. The decoys are pre-screened using anti-His antibody in an immunoprecipitation technique to ensure the His tag on the decoy molecule is accessible.

The decoys are next biotinylated using the biotinylation reagents sold by Thermo Scientific (Waltham, Mass.). The decoys are biotinylated on the end of the molecule other than where the His tag is attached. For example, if the His tag is attached to the N' terminus of the decoy, that decoy is biotinylated on its C'terminus (e.g., using the EZ-LINK Alkoxyamine-PEG-Biotin kit from Thermo Scientific). Likewise, if the His tag is attached to the C' terminus of the decoy, that decoy is biotinylated on its N'terminus (e.g., using the EZ-Link Sulfo-NHS-LC-Biotin Kit from Thermo Scientific).

Competitive assay formations will be established in the AMMP technique using the ViBE instrument with each of the decoys in a configuration shown in FIG. 15. In FIG. 15, the magnetic beads are coated with protein A, which has high affinity for the Fc region of the anti-His antibodies. The sensor surface is coated with streptavidin which will specifically bind the biotinylated terminus of the decoy.

The samples will be added to the competitive assay formation of FIG. 15 and those that can break (i.e., disrupt) the competitive assay formation and thus reduce the output signal are identified as high quality biological molecules (i.e., high quality human IL-2, high quality human CD2, or high quality human syk kinase).

If the amount of the high quality biological molecule in the sample is desired, the mixture can be 'spiked" with a known amount of free (i.e., non-bound) anti-His his tagged antibody. The anti-His His tagged antibody will bridge the beads and the sensor and thus make a competitive assay formation while the high quality biological molecule will disrupt the competitive assay formation. The amount of the high quality biological molecule in the sample can thus be quantitated based on the amount of the anti-His His tagged antibody spiked (i.e., added) into the mixture.

Example 3

HIS-Beads AMMP Assay Configuration for an Immunometric Inhibition Assay that Identifies Expressed HIS-Accessible Protein In another variation, using the AMMP method, clonal cell lines expressing a high quality biological molecule can quickly be selected based on the presence of a high quality biological molecule in that cell (or conditioned media in which the cell has been grown if the biological molecule is secreted).

Lipocalin1 protein (Sino Biological, Beijing China) was selected as the secondary HIS fused protein with HIS tag located at the C terminus. The Lipocalin1 protein is called a decoy herein because it serves as the positive control in the competitive formation. A decoy such as lipocalin1 protein may be approximately 20 kDa in size, are soluble and hydrophilic in nature, have a low propensity for aggregation. Although Lipocalin1 (LCN1/VEGP/Lipocalin-1 Protein) is used in this non-limiting example, other non-limiting decoy proteins include whale myoglobin and the human ubiquitin-conjugating enzyme E2w.

Note that the terms "decoy" and "tracer are used interchangeably throughout this document. Both terms mean a protein or peptide (e.g., a 20 kDa protein), where one portion of the protein is a tag portion that can be specifically bound by a binding agent and another portion of the protein is an anchor portion that can be attached (e.g., covalently or non-covalently via a bridging molecule such as an antibody) to a solid support such as a magnetic bead. For example, the anchor portion may comprise the N-terminus or free NH3 groups of lysine residues. Using ammonium sulfate mediated nucleophilic attack, the primary amine groups (e.g., from the N-terminus of polypeptide or from lysine residues in the anchor portion) can be conjugated to epoxy-sites on solid surfaces. Alternatively, EDC-carbodiimide conjugation of carboxylic acids (polypeptide C-terminus) can be used to attach the decoy (where in this embodiment, the anchor on the decoy is at the C-terminus of the protein) to carboxylic-sites on a solid phase.

In some embodiments, the decoy may be the precursor of a mature biological molecule, where the mature biological molecule is located as a portion of the precursor. For example, a peptide hormone is often produced as a precursor molecule. The mature peptide hormone is eventually cleaved from the precursor, thereby activating the mature peptide hormone.

For the lipocalin1 protein decoy, a fragment of a larger protein and was selected due to its soluble hydrophilic nature with low propensity for aggregation. Sufficient HIS tag was selected for recognition by anti-pentaHIS antibody. In this example, the Lipocalin1 was loaded onto M280 epoxy beads (LIFE Technologies) at 20 micrograms per milligram of beads, overnight at 37 C according to recommended protocol supplied by the vendor. Lower bead loadings are possible for more sensitivity in the assay.

The HIS tagged lipocalin1 protein was used as a standard for reference calibration purposes. In the assay 500 nM titrated down in serial factors of three was used to generate the reference standard curve.

Mouse anti-pentaHIS antibody (Qiagen) was fluorescein labeled (Pierce (a Thermo Scientific company)) for use in the assay. Approximately 2 fluorescein moieties per antibody were achieved for use in the assay. Fluorescein antibody is diluted in 1× Phsophate Buffered Saline with 10% Fetal Bovine Serum. Twenty microliters of the working concentration of antibody is added to 80 microliters of sample (or standard) to give a first incubation concentration of 600 nanograms per milliliter of antibody. Incubation of sample (or standard) with antibody is timed at 60 minutes while shaking on a plate shaker (set at ~500 rpm with ~1 mm orbital radius)

Beads are likewise diluted to a working concentration in 1× Phosphate Buffered Saline with 10% Fetal Bovine Serum. In a second step, beads are added to the sample plus antibody mixture, to a final concentration of 1.5e5 beads per milliliter, and the total mixture incubated for a further 30 minutes on the plate shaker prior to readout.

Figure 16:
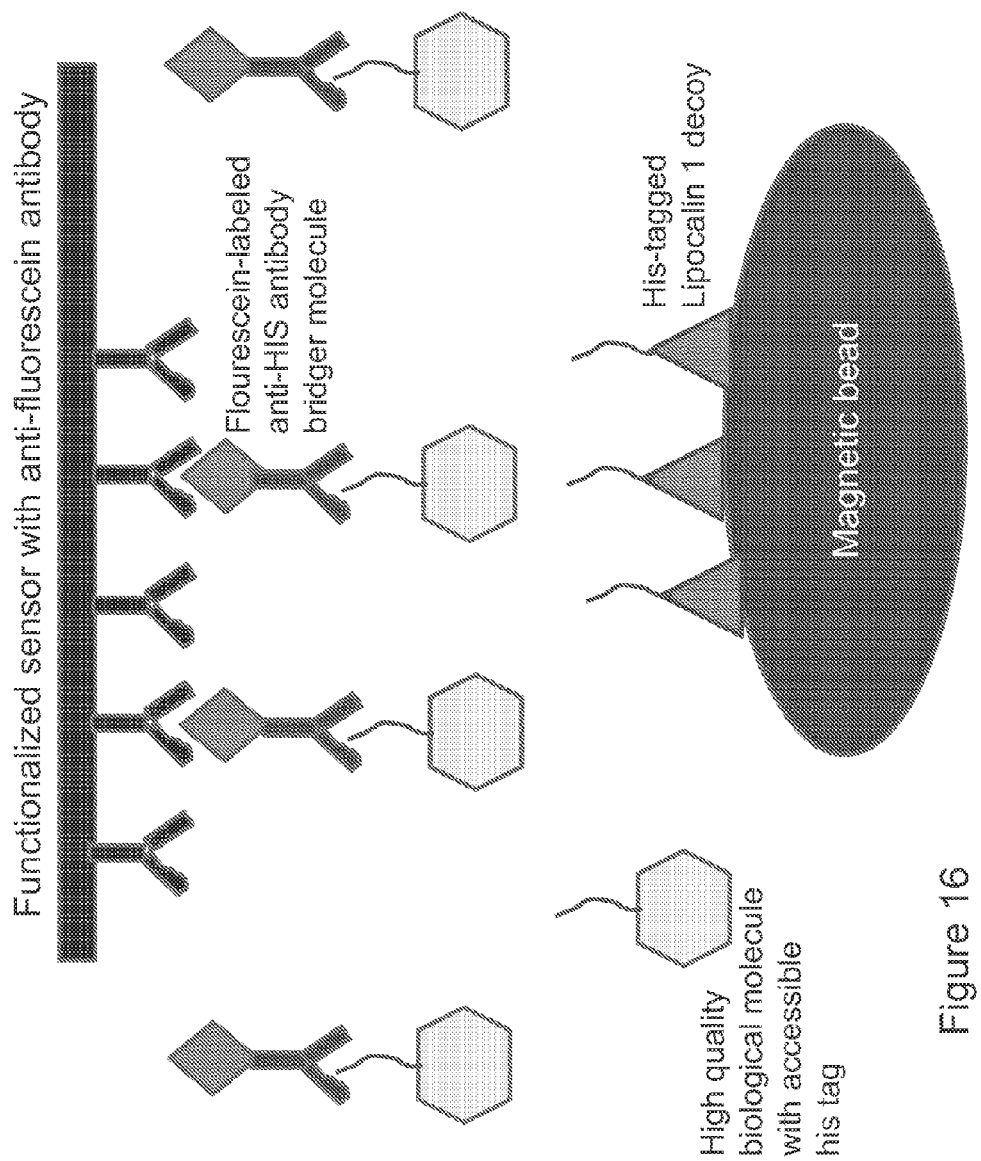
FIG. 16 is a schematic diagram showing the competitive assay formation of FIG. 3 being disrupted by a high quality biological molecule with an accessible His tag. As noted in the FIG. 16, the disruption can be from the complex of the high quality biological molecule:bridger molecule binding to the sensor, or the high quality biological molecule:bridger molecule complex not binding to the sensor. In either scenario, the bead no longer specifically binds to the sensor, thereby changing the output signal of the sensor.

A competitive assay formation as shown in FIG. 3 was established. In one embodiment of FIG. 3, the target-specific antibodies that are attached to the sensor are anti-fluorescein antibodies. In this configuration, the decoy (e.g., a His-tagged lipocalin1) is attached (e.g., coated onto) to the magnetic bead such that all or most (e.g., over 50%) of the his tags of the decoys are accessible (e.g., accessible for binding by an anti-His antibody that is attached to the target which, in this case, is fluorescein). The bridger molecule comprising a tag-specific antibody attached to target molecule that bridges the sensor and the magnetic bead is a fluorescein labeled anti-HIS antibody (the fluorescein is shown as a green diamond in FIGS. 3 and 16). When mixed with sample suspected of comprising a biological molecule to be tested (in this case a His tagged fusion protein, shown as a yellow hexagon with the His tag shown in blue in FIG. 16), the exposed HIS tag from the His-tagged lipocalin 1 on the beads competes with the His tag on the high quality biological molecule in solution (yellow hexagon) for specific binding by the fluorescein-labeled anti-HIS antibody. When low/no native fusion protein (i.e., an incorrectly folded fusion protein) is present, the competitive assay formation remains formed giving high assay signal. However, when a correctly folded fusion protein (i.e., a high quality biological molecule) is present, the antibody is bound in solution to the high quality biological molecule and low/no amounts are available to bridge the beads to the sensors giving low assay signal. If a known amount of the bridger molecule (i.e., an anti-His antibody attached to the target molecule) is present, the relative amount of the high quality biological molecule can be determined by calibrating the output signal in the presence of the reference high quality biological molecule versus the output signal generated in the absence of the reference high quality biological molecule.

To test the samples, lysate samples were thawed and spun in a centrifuge at 14000 g for 10 minutes. Supernatant was then diluted 1:80 prior to serial dilution three fold in 1× Phosphate buffer with 0.45M NaCl and 10% MPER (Sigma). Of course, it should be noted that the supernatant can be diluted by other degrees (e.g., by 1:10) or not diluted at all. Standards were diluted in serial factors of three in the sample diluent starting at 500 nanomolar. Eighty microliters of neat or diluted samples and standards was used in each reaction.

Beads only, and beads+antibody controls were run in sample diluent. These gave high and low signal levels for the assay respectively and were used for analysis by bounding the fitting of dilution curves for each sample.

Anti-flourescein coated sensors were hydrated (by an automated protocol in the BioScale ViBE instrument) with Phosphate Buffered Saline 1% Tween20 with (1% FBS final concentration) wash buffer.

Post steps of 60 minute incubation with antibody and subsequent 30 minutes incubation with beads samples were readout by the BioScale ViBE instrument. The ViBE instrument runs a detection protocol as previously described in U.S. Pat. Nos. 7,300,631; 7,611,908; 7,598,094; 7,615,381, 7,629,137; and US Patent Publication No. US2007/0117214A1.

Sample was loaded into the ViBE detection cartridge and is flowed by the sensors at 70 ul/min in the presence of magnetic field. Beads are drawn to the sensor surfaces form the flowing sample. After about 30 seconds, sample flow is exchanged with wash buffer and bead loaded sensors are washed at about 200 ul/min in the presence of magnetic field. The magnetic field is removed and the sensors washed with sensor wash buffer at 70 ul/min for a period of about 1 min after which the sensor signal, relative to the total sensor loading prior to magnet field removal, is recorded. The signals from unknown samples are compared to reference calibration to give a referenced quantity of measured analyte.

Results from Test Samples

Two sets of proteins were expressed in *E. coli* and insect (SF9) cell lines. Assay results for the *E. coli* expressions are shown in FIG. 17, with AMMP signal plotted versus the log of the dilution factor for the sample. As shown in FIG. 17, high signal level is set by beads+antibody alone data (i.e., His tagged lipocalin 1 coated beads plus fluorescein-labeled anti-His antibody) while low signal is set by beads alone data. Proteins, including the lipocalin1 standard show self similar signal versus dilution. Clearly by the nature of the curves, there appears to be more of the PD protein. The concentration, based on the nature of the curves shown in FIG. 17 is PD amount is greater than (i.e., >) the PE amount, which is greater than (i.e., >) the PC amount which is approximately equal to the amount of PF, which is greater than the amounts of PA and PB (which are approximately equal).

These data are fit with four or five-parameter logistic fits (PL4, PL5 may also work, see BIO-RAD application note:

Principles of Curve Fitting for Multiplex Sandwich Immunoassays, Rev B. Diana Davis, PhD, Aiguo Zhang, PhD, Chloe Etienne, Ivan Huang, and Michele Malit, Bio-Rad Laboratories, Inc., 2000 Alfred Nobel Drive, Hercules, Calif. 94547 USA). Further references for curve fitting and attaining IC50's include Nix B and Wild D, "Calibration curve-fitting", pp 198-210 in *The Immunoassay Handbook*, $2^{nd}$ (David Wild, ed), Nature Publishing Group, New York, N.Y. (2001).

Analytically the IC50 (inhibitory concentration to 50%, see *The Immunoassay Handbook*) is calculated for the standard knowing the concentrations of standard used in the assay. Reference IC50's for each of the unknown samples is then calculated visa vi the following relations:

Quantitative Aspects

Since antibody binding to bead is measured, all curves are parallel, with identical MAX (maximum) and MIN (minimum) values, so the formula $$[unk]=[std]*(IC50unk/IC50Std)$$

measures IC50 shift, and returns results in nM concentrations of unknown. The IC50LCN1 is approximately equal to 60.

Alternatively, the formula $$[unk]=[std]*10^{(log\ IC50unk-log\ IC50std)}$$

can be used

These relative IC50's give a number for each expression relative to the dilution characteristic of the standard. The number calculated is robust to variations as the curves are fit across dilutions. They are faster to refer to than sensitivity which by definition includes background noise which differs from lysate to lysate. In general, the IC50 method is more precise than reading numbers of the curves and comparing them.

For the *E. coli* lysate data, relative rankings of these expressed proteins are given in Table 3.

according to calculated IC50 based on dilution factor relative to the lipocalin1 standard (where the 1050 is approximately 60). These ranking agree completely with downstream purified product ranking and thus show that the upstream AMMP method can be powerful for selecting high performing cell lines while eliminating those that underperform. Further the relative numerical rank allows for further optimization of expression conditions by providing a reference value for comparison of conditions.

In addition to *E. coli* cell lines, a set of proteins were investigated from insect SF9 cell expression constructs. These data are shown in FIG. 18. Dilution curves fit to the data show that the amount of P1 is greater than (i.e., >) the amount of P4 which is greater than (i.e., >) the amount of P6 which is greater than (i.e., >_the amount of P2 which is greater than (i.e., >) the amount of P3 which is greater than (i.e., >_the amount of P5 in terms of available material that reduces the signal in the assay.

Again relative IC50's were calculated using PL4 fits to the dilution data. These data are given in Table 4 along with the AMMP ranking derived from them. As with the *E. coli* data, this ranking agrees completely with post purification product measured yields allowing for pre purification identification of high and low performing cell lines and expressions. In this case the proteins expressed span a large range

TABLE 3

Relative AMMP ranking for six different proteins expressed from *E. coli*.

| ID | PC | PA | PB | PE | PF | PD |
|---|---|---|---|---|---|---|
| MW (daltons) | 36000 | 27400 | 50100 | 31700 | 35600 | 59300 |
| His orientation | C' | N' | N' | C' | N' | N' |
| Wet weight (g) | 0.9 | 0.9 | 0.8 | 0.4 | 1.0 | 0.9 |
| Total Protein (ug/ml) | 11.45 | 8.14 | 11.96 | 9.42 | 10.06 | 25.60 |
| AMMP ® Rank | 4 | — | — | 2 | 3 | 1 |
| IC-50 | 1.616 | 0.097 | 0.089 | 8.902 | 1.683 | 240.3 |

Table 3 shows that the expressed proteins, that span a reasonable size range, from 27 to 60 kDa, can be ranked of size, 35 kDa to 240 Kda, showing that the method is somewhat size independent.

TABLE 4

Relative AMMP ranking for six different proteins expressed from SF9 (insect) cells.

| ID | P1 | P2 | P3 | P6 | P4 | P5 |
|---|---|---|---|---|---|---|
| MW (daltons) | 37100 | 48600 | 35600 | 31700 | 121100 | 235000 |
| His orientation | N' | C' | C' | N' | C' | N' |
| Cells (x1e6) | 191 | 124 | 97 | 105 | 122 | 99 |
| Protein (mg/ml) | 12.30 | 14.60 | 11.20 | 18.30 | 10.50 | 10.60 |
| AMMP Rank | 1 | 4 | — | 3 | 2 | — |
| IC-50 | 27.23 | 1.407 | 0.955 | 6.201 | 17.13 | 0.102 |

Relative ranking of unknown high quality biological molecules can also be achieved with straight forward quantification from a standards curve. Reference standards curves are shown in FIGS. 17 and 18 where the free form (i.e., unbound to the beads) of the tagged decoy molecule was used to register signal across a concentration range. Equivalent background levels and saturating signal levels for all the biological molecules tested (and the different biological molecule production constructs tested) is a feature of this assay design and allows for quantification directly from the standards curve.

Relative unknown quantities, when corrected for dilution, can be recovered from the reference standard curve when in range by comparing the signal achieved for the unknowns with a 5PL curve fit to the standards.

Note that to generate the standard curves (depicted by the black circles and the black dashed lines in FIGS. 17 and 18), the standards were prepared in "null lysates' (i.e., non-transfected host cells, e.g., E. coli lysates or Sf9 lysates at 1 uM concentration, and then divided into 20 microliter, single use aliquots, and stored at −80 C for later use. All the calculations were done on molar basis (as opposed to weight-per-ml) concentrations. Standards were treated as normal samples—same numbers of beads, same concentration of bridger molecule (i.e., fluorescein-labeled anti-HIS antibodies), same incubation times. The only difference was that standards were serially diluted through at least 5-, and preferably 8-places, while other samples shown might be single dilutions, replicates, etc.

For the above data, each plate contained at least one 8-place standard curve (8 wells) and at least two wells each of MAX (beads plus antibody, no free decoy, and no sample), MIN (beads, no antibody, no free decoy), and optional sample-specific non-specific binding (beads plus sample, no antibody).

For 4-parameter, relative potency analysis—samples (as well as standards) are loaded to plates as 8-place serial dilutions, and resulting AMMP signals are plotted vs log (dilution). The resulting curves are fit to the logistic model $$[y=MIN+((MAX-MIN)/\text{signal}-MIN))/(1+((x/ED50)^{\text{HillSlope}})].$$

For this analysis, standards and samples share the same MAX and MIN values, and the Hill Slopes are identical—thus the resulting lines are parallel. Consequently, differences in concentrations are reflected as 'ED50'-shifts. Since the initial concentration of the standard is a known molarity, it can be concluded that the initial concentration of the standard divided by the ED50 of the standard equates to the initial concentration of the unknown (sample) divided by its ED50, or $$[\text{unknown}]=[\text{standard}]\times(ED50_{unknown}/ED50_{standard}).$$

Therefore, the potency of the unknown sample relative to the standard is exactly equal to the ED50 ratio of the two moieties.

For a 5-parameter, direct quantitation, everything was done as above, except that resulting AMMP signals are plotted vs the logarithm of molar concentrations of the standard (instead of against the dilution factors). After solving for the 5-parameters, the observed AMMP signals can be back-calculated or read directly from the concentration-based standard curve.

Uniqueness of Results

These results are unique in that they are easy to achieve and give accurate ranking of expressed protein quantity relative to downstream post purification measures. Various other methods of achieving similar results are either cumbersome (western) or inaccurate (mass and size dependent). The AMMP method is simple, takes hours rather than days and accurate. The method is sensitive in that nanomolar quantities of reference material are readily identified. Other techniques require micromolar quantities of material (the reference is diluted by as much as 100-1000 from 500 nanomolar starting concentration) to make measurements.

Example 4

Detecting the Presence of an Active Peptide Hormone

Using the methods described herein, the presence of an active peptide hormone (as opposed to an inactive precursor) can be detected.

Peptide hormones, including prolactin, vasopressin, and oxytocin, are synthesized as inactive precursors but become active when cleaved from their zymogens (i.e., their inactive precursors). In this example, active oxytocin (a non-limiting peptide hormone) is detected.

Oxytocin is a nona-peptide (9-amino acid) pituitary hormone which acts, primarily, in the vertebrate central nervous system. Oxytocin levels appear to be important in the development of complex social behaviors, and more recent findings suggest anti-inflammatory activities associated with cytokine synthesis and release. Accurate measurement of this analyte is problematic on several fronts. First, the oxytocin molecule is well-conserved in vertebrates, making its native immunogenicity poor at best. In order to develop antibodies with meaningful affinities and specificities, it is likely that at least some chemical modification of the analyte (amino acid substitution or extension, hapten (amino acid substitution or extension, haptenylation, or conjugation to larger, immunodiverse molecules, etc.) will be essential. Moreover, antibodies with appropriate and adequate specificity are likely to have relatively large KD ('off-rates'). The lower the KD, the higher the affinity of the antibody. For antibodies with a large (i.e., high) KD for oxytocin, the antibodies will be difficult to use in methods with vigorous washing steps (e.g., to control or minimize non-specific binding). In addition, since oxytocin is so small (i.e., only 8-9 amino acids in length), it is too small to support binding by more than one single antibody at a time; thus, sandwich-based assays are unlikely to succeed.

The physical state of circulating oxytocin remains unclear. Although it has become clear that oxytocin and neurophysin I are encoded from a single genomic sequence (NP-000915—oxytocin prepropeptide), the details of the processing steps required to cleave oxytocin from its precursor are unknown, but thought to occur during axonal transport. Unfortunately, neurophysin I is also characterized as a 'chaperone' or 'carrier' protein, suggesting that it may, under certain circumstances, recombine and circulate with the cleaved oxytocin molecule. Thus, oxytocin may circulate as a free nonapeptide (MW≈1000 daltons), as a dissociable complex with neurophysin I (MW≈10,000 daltons), or as the uncleaved prepropeptide (MW≈11,000 daltons), along with related degradation products.

One frequently used assay for circulating oxytocin levels involves significant sample preprocessing (typically, solid phase extraction on C-18 columns), followed by LCMS techniques. Using these techniques, normal levels of the nonapeptide oxytocin are reported in the range of 1-20 pg/ml (1-20 pM) for the nonapeptide. Unfortunately, neither the RIA (commercially available from Phoenix Pharmaceuticals, Burlingame, Calif.) nor the EIA techniques (commercially available from several vendors including Enzo Life Sciences, Farmingdale, N.Y.) correlate with each other or with LCMS-obtained values for identical serum/plasma samples. The immunoassays cited above measure the ability of serially diluted serum/plasma samples to inhibit the binding of relatively high affinity (low off-rate) polyclonal rat, rabbit or goat antibodies to labeled (biotinylated-, isotopically- or fluorescein-labeled) synthetic nonapeptide. Little is published on the characterization of these immunological reagents, particularly with regard to specificity and selectivity of binding.

Oxytocin is "posterior pituitary hormone which is synthesized as an inactive precursor in the hypothalamus along with its carrier protein, Neurophysin I. Together with neurophysin, it is packaged into neurosecretory vesicles and transported axonally to the nerve endings in the neurohypophysis, where it is either stored or secreted into the bloodstream. The precursor (i.e., the zymogen) appears to be activated while being transported along the axon to the posterior pituitary".

This situation is analogous, if not identical, to that observed in the development assays detecting accessibly tagged biological molecules described above. The precursor molecule, prepro-oxytocin, is commercially available (catalog number TP324226, Origene Technologies, Rockville, Md.), and contains a 19-amino acid signal sequence, followed by the oxytocin nonapeptide sequence ($aa_{20-29}$), and the 9 Kd, C-terminal sequence comprising the 'carrier' protein, neurophysin I.

Accordingly, an immunometric AMMP assay for oxytocin is modeled on the assays described above by substituting preprooxytocin for the decoy comprising a tag portion attached to an anchor portion, where the anchor portion is attached to a solid support. For example, the preprooxytocin molecule will be substituted for the M280 expoxy bead-attached HIS tagged lipocalin1 protein described above in Example 2 and depicted schematically in FIG. 16. A fluorescently-conjugated anti-oxytocin antibody (i.e., that specifically bind to mature oxytocin having the amino acid sequence: CYIQNCPLG) is then used as the bridger molecule in place of the fluorescently-conjugated mouse anti-pentaHIS antibody bridger molecule described in the above examples.

For this assay, the following methods will be used.
Immobilized Target:

The target-of-choice for this assay is bead-immobilized oxytocin prepropeptide (the uncleaved precursor molecule having the amino acid sequence: MAGPSLACCLLGLLA-LTSACYIQNCPLGGKRAAPDLDVRKCLPCGPGGK-GRCFGPNICC AEELGCFVGTAEALRCQEENYLPSPC-QSGQKACGSGGRCAVLGLCCSPDGCHADPACD AEATFSQR (SEQ ID NO: 1; GenBank Accession No. NM-000915). The protein is commercially available as an affinity-purified protein from HEK293 cells transiently transfected with the TrueORF clone, RC224226 (OriGene Technologies, Inc; CatNo TP324226). In this prepro-form, oxytocin is presented as $aa_{(20-28)}$ in the 11 Kd protein sequence. The remaining amino acids comprise oxytocin's chaperone or carrier protein, neurophysin I, which is anticipated to circulate in near-equimolar concentrations to the concentration observed for oxytocin.

In some embodiments of this methods, the antibody that specifically binds to mature oxytocin (i.e., CYIQN CPLG-NH$_2$) do not specifically bind to the closely related peptide hormone vasopressin (CYFQNCPRG-NH$_2$) and/or its prepro-form, neurophysin II. Consequently, these molecules must be considered in developing appropriate negative controls. Some non-limiting commercially available mature oxytocin-specific antibodies that may be used in this method include the Oxytocin RabMab #3371-1 (commercially available from Epitomics, Burlingame, Calif.), the Oxytocin MouseMab 4G11, #Ab78364 (commercially available from Abcam, Cambridge, Mass.) and the Oxytocin MouseMab 2Q85, #O8250-10 (commercially available from, USBiological, Swampscott, Mass.). Additionally, a wide variety of polyclonal antisera are available from rabbit, rat, goat and sheep. These may also be tested for specificity and selectivity for possible inclusion in the assay.

The anti-oxytocin antibody will be conjugated to fluorescein to make the bridger molecule according to standard methods. Similarly, the preprooxytocin and neurophysin I will be conjugated to beads, each at 5-, 10-, and 20 μg/mg beads), and to fluoresceinate up to 8 distinct antibody preparations. From these preparations, the bead:antibody pairs which deliver maximum signal with minimal non-specific ('bead-only') background are selected. In addition, the bridger molecules (i.e., the fluorescein-conjugated anti-oxytocin antibodies) will be screened (e.g., by Western blotting analysis) to select for those bridger molecules comprising antibodies that specifically bind to preprooxytocin, but do not specifically bind to neurophysin I, and ensure that the binding of the antibody portion of the bridger molecule to preprooxytocin is inhibited by recombinant oxytocin.

Next, the dose-dependent inhibitory effect of recombinant oxytocin on the binding of the selected, labeled antibody to bead-immobilized preprooxytocin will be determined in order to establish a standard curve with upper asymptote in excess of 100 pM, and lower asymptote approaching the 1 pM sensitivity target of the assay. Initial studies will be performed in standard dilution buffers, then fine tuned to use the serum cytokine dilution buffer (BioScale, Inc, Lexington, Mass.). AMMP methods will reflect those used in Examples 1 and 2 above, and will be modified as necessary to minimize background while maximizing signal. Additional bead preparations may be required at adjusted target protein densities in order to reach desired assay LOD values.

Upon completion of initial optimization studies, the resulting assay will be deployed to test various serum and plasma samples for the levels of circulating oxytocin. These verification studies will include preliminary spike recoveries (using recombinant oxytocin) to assess linearity of response in the assay.

Following verification, the assay is ready to begin testing for the level of circulating oxytocin in a sample.

Example 5

Detecting the Presence of an Active Coagulation Protein

Coagulation is the process by which blood forms fibrin-containing clots. The process is effected by members of the coagulation cascade, most of which are serine proteases although some (e.g., Factor VIII and V are glycoproteins and factor XIII is a granslutaminase. There are actually two pathways, namely the tissue factor pathway and the contact activation pathway, that both activate the final common pathway of factor X, thrombin, and fibrin.

In some individuals, members of the coagulation cascade are aberrant. For example, patients with Haemophilia A lack functional factor VIII. Factor VIII acts as a cofactor for factor IXa that will convert inactive zymogen factor X to active mature protein factor Xa. Using the methods described herein, a patient lacking active factor Xa in his or her blood following an injury (e.g., a broken blood vessel such as a superficial cut) may be detected. The patient then be further screened to determine if that patient has hemophilia A.

Accordingly, a competitive assay formation is designed using the zymogen factor X, a sensor-bound antibody that specifically binds to a portion of factor X that does not include the factor Xa portion, and a bead-bound antibody that specifically binds to the factor Xa portion of the factor X zymogen. Next, samples from the patient (e.g., a blood sample) taken before and after the patient has an injury added to the competitive assay formation to see if the sample contains any free factor Xa. Free factor Xa will disrupt the competitive assay formation.

A patient found to lack free factor Xa following injury may be subjected to further testing to determine if that patient has hemophilia A.

Example 6

Detecting the Aggregates of Expressed Recombinant Biological Molecules

Often, a recombinant biological molecule forms aggregates or clumps during its production and/or purification. Often, these aggregates are missed because they do not appear to be correctly folded. Furthermore, in certain conditions, it may be that an aggregated biological molecule is more desirable than a monomeric biological molecule (e.g., the aggregate may come from a recombinant cell line that produces more of the biological molecule. In some embodiments, the aggregated biological molecule may be de-aggregated during further purification.

Accordingly, the method described herein can be used to distinguish non-aggregated versus aggregated recombinant biological molecule.

For example, if a protein is expressed in one cell expression system (e.g., a COS cell expressions system), that expression system might cause clumping or aggregates where another cell expression system (e.g., an Sf9 insect cell expression system) does not. Similarly, certain cell media or certain lysis conditions may result in clumping when other cell media or lysis conditions do not. For example, a gentle cell lysis buffer (e.g., the M-PER mammalian protein extraction reagent (Thermo Scientific, catalog number 78501) or a buffer using a mild detergent such as 1% Nonidet P-40 (NP40) that can be used to lyse COS cells expressing a recombinant cytosolic protein of interest may result in clumping and aggregates of that protein of interest, whereas a harsher cell lysis reagent (e.g., a RIPA lysis buffer such as the RIPA lysis buffer sold by Thermo Scientific, catalog no. 89900) used on the same cells may result in recombinant protein that does not aggregate. The type of cell culture media, or the amount or type of serum in that media may also affect clumping. For example, recombinant COS cells grown in RPMI media with 10% calf serum (i.e., not fetal) may produce a secreted recombinant biological molecule that forms clumps in the media, whereas those cells grown in DMEM media with 10% fetal bovine serum may produce a secreted recombinant biological molecule that does not clump.

For these methods, the competitive assay formations described above can be used to detect clumping or aggregated recombinant proteins. If such aggregates are not desired, growth conditions, lysis conditions, and/or cell type (or even a different clone) can be utilized to produce non-clumping recombinant protein.

The methods described herein are useful in detecting aggregates.

For these studies, the recombinant cell lines described in Example 2 are grown in RPMI media with 10% calf serum or DMEM media with 10% fetal bovine serum. For the transmembrane and cytosolic proteins (i.e., the CD2 and the syk kinase proteins), different cell lysis conditions are used.

Samples are taken from the different cells grown and/or lysed in the various different conditions.

A competitive assay formation such as that depicted in FIG. 3 is established. As can be seen, an aggregate of high quality biological molecules with multiple accessible His tags will compete with the beads for binding to the sensor and thus reduce the AMMP output signal, giving a positive result. The amount of the decrease in the signal will be reflective of the number of accessible His tags are present in the sample. The presence of the aggregate can be confirmed, for example, in an immunoprecipitation assay using an anti-target antibody to pull down the aggregated protein.

The various growth conditions, lysis conditions, cell lines, etc. can be selected for further propagation of the selected cell clone based on whether or not aggregates are detected.

While the invention has been described with particular reference to the illustrated embodiments, it will be understood that numerous modifications thereto will appear to those skilled in the art. Accordingly, the above description, the following claims, and accompanying drawings should be taken as illustrative of the invention and not in a limiting sense.

The invention claimed is:

1. A method for detecting a high quality biological molecule in a sample, the method comprising:
   (a) introducing a fluid comprising a plurality of magnetic particles, a decoy comprising an anchor labelled with a tag, and a sample suspected of containing a high quality biological molecule labelled with the tag, wherein the tag of the high quality biological molecule is accessible, into a fluid chamber, said magnetic particles being coated with a first binding agent that specifically binds to the tag, wherein at least one surface of the fluid chamber comprises a flexural plate wave device capable of emitting an output signal, wherein the flexural plate wave device has a membrane that is capable of vibrating, and wherein a second binding agent that specifically binds to the anchor of the decoy is attached to the membrane;
   (b) applying a retractable source of magnetic flux positioned external to the fluid chamber close to the membrane to create a significant magnetic field gradient to attract at least one of the plurality of magnetic particles in the fluid toward the membrane;
   (c) flowing a solution through the fluid chamber to remove magnetic particles not specifically bound to the membrane by the second binding agent;
   (d) obtaining an output signal by said flexural plate wave device that corresponds to a number of the magnetic particles specifically bound to the membrane; and
   (e) comparing the output signal to a control output signal obtained by performing steps (a)-(d) in the absence of the sample suspected of containing the high quality biological molecule;
   wherein a change in the output signal as compared to the control output signal indicates that a high quality biological molecule is present in the sample.

2. The method of claim 1, wherein the high quality biological molecule labelled with the tag is biologically functional or is expressed by a cultured cell.

3. The method of claim 1, wherein the high quality biological molecule is a protein, is a lipid, or is a carbohydrate.

4. The method of claim 2, wherein the cell is a prokaryotic cell, a eukaryotic cell, or a mammalian cell.

5. The method of claim 4, wherein the cell is selected from the group consisting of a COS cell, a CHO cell, a HeLa cell, a Jurkat cell, a Daudi cell, a 293 cell, an SP2/0 cell, a HT-1080 cell, an NSO cell, a PER.C6 cell, an Sf9 cell, and a yeast cell.

6. The method of claim 1, wherein the tag is selected from the group consisting of a His tag, a GST tag, a FLAG tag, a V5 tag, a myc tag, and an HA tag.

7. The method of claim 1, wherein the high quality biological molecule is a secreted molecule, a cytosolic molecule or a transmembrane molecule.

8. The method of claim 1, wherein the method is carried out using AMMP technology or using a ViBE instrument.

9. The method of claim 1, wherein the method further comprises determining a quantity of the high quality biological molecule, the method further comprising diluting the amount of the sample introduced into the fluid chamber in step (a) and calibrating the output signals to determine the quantity of the high quality biological molecule present.

10. The method of claim 1, wherein the change is a decrease.

11. A method for detecting a high quality biological molecule in a sample, the method comprising:
   (a) introducing a fluid comprising a plurality of magnetic particles, a decoy comprising labelled with a tag, wherein the decoy is a zymogen of a mature protein and the tag is the mature protein, and a sample suspected of containing a high quality biological molecule labelled with the tag, wherein the tag of the high quality biological molecule is accessible, into a fluid chamber, said magnetic particles being coated with a first binding agent that specifically binds to the tag, wherein at least one surface of the fluid chamber comprises a flexural plate wave device capable of emitting an output signal, wherein the flexural plate wave device has a membrane that is capable of vibrating, and wherein a second binding agent that specifically binds to the anchor of the decoy is attached to the membrane;

(b) applying a retractable source of magnetic flux positioned external to the fluid chamber close to the membrane to create a significant magnetic field gradient to attract at least one of the plurality of magnetic particles in the fluid toward the membrane;

(c) flowing a solution through the fluid chamber to remove magnetic particles not specifically bound to the membrane by the second binding agent;

(d) obtaining an output signal by said flexural plate wave device that corresponds to a number of the magnetic particles specifically bound to the membrane; and (e) comparing the output signal to a control output signal obtained by performing steps (a)-(d) in the absence of the sample suspected of containing the high quality biological molecule;

wherein a change in the output signal as compared to the control output signal indicates that a high quality biological molecule is present in the sample.

12. The method of claim 11, wherein the mature protein is a peptide hormone, a member of a complement cascade, a member of a coagulation cascade, a caspase family member, or a digestive protein.

13. The method of claim 12, wherein the peptide hormone is oxytocin, prolactin, vasopressin, somatostatin, insulin, or adrenocorticotropic hormone.

14. The method of claim 12, wherein the member of the complement cascade is selected from the group consisting of a C1r protein, a C4b protein, a C2b protein, a C5a protein, and a C5b protein.

15. The method of claim 12, wherein the member of the coagulation cascade is selected from the group consisting of a factor XIIa protein, a factor XIa protein, an IXa protein, a Xa protein, a thrombin protein, a fibrin protein, and a factor XIII protein.

16. The method of claim 12, wherein the caspase family member is caspase 5, caspase 7, caspase 9, or caspase 2.

17. The method of claim 11, wherein the high quality biological molecule is a protein, is a lipid, or is a carbohydrate.

18. The method of claim 11, wherein the method is carried out using AMMP technology or using a ViBE instrument.

19. The method of claim 11, wherein the method further comprises determining a quantity of the high quality biological molecule, the method further comprising diluting the amount of the sample introduced into the fluid chamber in step (a) and calibrating the output signals to determine the quantity of the high quality biological molecule present.

20. The method of claim 11, wherein the change is a decrease.

* * * * *